(12) United States Patent
Ostermaier et al.

(10) Patent No.: US 11,401,321 B2
(45) Date of Patent: Aug. 2, 2022

(54) METHOD FOR DETERMINING MUTATEABLE LIGAND-GPCR BINDING AT SINGLE AMINO ACID RESOLUTION AND PAIRS OF MUTATED LIGAND AND GPCR

(71) Applicant: PAUL SCHERRER INSTITUT, Villigen Psi (CH)

(72) Inventors: Martin Ostermaier, Waldshut-Tiengen (DE); Gebhard Schertler, Hertenstein (CH); Joerg Standfuss, Brugg AG (CH)

(73) Assignee: Paul Scherrer Institut, Villigen (CH)

( * ) Notice: Subject to any disclaimer, the term of this patent is extended or adjusted under 35 U.S.C. 154(b) by 818 days.

(21) Appl. No.: 14/897,728

(22) PCT Filed: May 27, 2014

(86) PCT No.: PCT/EP2014/060900
§ 371 (c)(1),
(2) Date: Dec. 11, 2015

(87) PCT Pub. No.: WO2014/198528
PCT Pub. Date: Dec. 18, 2014

(65) Prior Publication Data
US 2016/0139155 A1    May 19, 2016

(30) Foreign Application Priority Data

Jun. 11, 2013   (EP) ..................................... 13171505

(51) Int. Cl.
| C07K 14/705 | (2006.01) |
| C07K 14/72 | (2006.01) |
| G01N 33/74 | (2006.01) |

(52) U.S. Cl.
CPC ........... C07K 14/723 (2013.01); G01N 33/74 (2013.01); *G01N 2333/726* (2013.01); *G01N 2500/04* (2013.01)

(58) Field of Classification Search
None
See application file for complete search history.

(56) References Cited

U.S. PATENT DOCUMENTS

| 6,800,445 | B2 | 10/2004 | Palmer et al. |
| 6,893,827 | B1 | 5/2005 | Palmer et al. |
| 7,235,374 | B2 | 6/2007 | Palmer et al. |
| 7,678,539 | B2 | 3/2010 | Fang et al. |
| 8,785,135 | B2 | 7/2014 | Henderson et al. |
| 8,790,933 | B2 | 7/2014 | Weir et al. |
| 8,999,653 | B2 | 4/2015 | Zwier et al. |
| 9,260,505 | B2 | 2/2016 | Weir et al. |
| 9,587,014 | B2 | 3/2017 | Nitsch et al. |
| 2003/0157553 | A1 | 8/2003 | Berstein |
| 2005/0009204 | A1 | 1/2005 | Fang et al. |

FOREIGN PATENT DOCUMENTS

| JP | 2004504805 A | 2/2004 |
| JP | 2005515402 A | 5/2005 |
| JP | 2007530919 A | 11/2007 |
| JP | 2010521983 A | 7/2010 |
| JP | 2011508875 A | 3/2011 |
| JP | 2011529338 A | 12/2011 |
| WO | 0158923 A2 | 8/2001 |
| WO | 2008114020 A2 | 9/2008 |
| WO | 2009081136 A2 | 7/2009 |
| WO | 2013061163 A2 | 5/2013 |

OTHER PUBLICATIONS

Gurevich (1998) J. Biol. Chem. 273:15501-15506.*
Hirsch Joel A. et al.; "The 2.8 A Crystal Structure of Visual Arrestin: A Model for Arrestin's Regulation"; Cell Press; vol. 97; No. 2; pp. 257-269; ISSN: 0092-8674; DOI: 10.1016/50092-8674(00)80735-7; XP055088189; 1999.
Vishnivetskiy Sergey A. et al.; "Critical Role of the Central 139-Loop in Stability and Binding Selectivity of Arrestin-1"; Journal of Biological Chemistry; vol. 288; No. 17; pp. 11741-11750; XP002717058; 2013.
Kim Yong Ju et al; "Crystal structure of pre-activated arrestin p44"; Nature, London; vol. 497; No. 7447; pp. 142-146; DOI: 10.1038/nature12133; XP002717062; 2013.
V. Gurevich Vsevolod et al; "Mechanism of Phosphorylation-Recognition by Visual Arrestin and the Transition of Arrestin into a High Affinity Binding State"; Molecular Pharmacology; vol. 51; No. 1; pp. 161-169; ISSN 0026-895x; XP002717060; 1997.
Granzin Joachim et al; "X-ray crystal structure of arrestin from bovine rod outer segments"; Nature, London vol. 391; No. 6670; pp. 918-921; ISSN: 0028-0836; XP002717061; 1998.
Vishnivetskiy Sergey A. et al.; "Engineering Visual Arrestin-1 with Special Functional Characteristics"; Journal of Biological Chemistry; vol. 288; No. 5; pp. 3394-3405; XP002717059; 2013.

(Continued)

*Primary Examiner* — Michael D Pak
(74) *Attorney, Agent, or Firm* — Laurence A. Greenberg; Werner H. Stemer; Ralph E. Locher

(57) ABSTRACT

Method of determining GPCR and mutateable ligand binding ability, includes providing a well microtiter plate with well array having rows and columns, GPCR or rhodopsin in wells, and parent ligand mutant binding to GPCR when GPCR resides in conformation, contacting parent ligand mutants in wells with GPCR, coupling parent ligand to GPCR, and determining mutant ligand binding strength compared to standard parent ligand and GPCR by determining coupled mutant-GPCR complex in wells. Rhodopsin binding 403 mutants covering arrestin sequence provides functional 4th dimension arrestin crystal structures. Resulting single amino acid resolution functional maps reveal critical interactions in arrestin polar core and C-tail interrupted during activation. Amino acid patches reduce binding and act as direct binding rhodopsin interfaces. This and computational molecular docking active arrestin4 and light-activated rhodopsin develop arrestin-rhodopsin complex model. Combined mutants allow binding affinity modification and GPCR-ligand complex stability for diagnostics or intervention.

4 Claims, 9 Drawing Sheets

Specification includes a Sequence Listing.

(56) References Cited

OTHER PUBLICATIONS

Chen Keqin et al.: "Tuning the activity of an enzyme for unusual environments: Sequential random mutagenesis of subtilisin E for catalysis in dimethylformamide", Proceedings National Academy of Sciences PNAS, 19930615 National Academy of Sciences, US, vol. 90, No. 12, Jun. 15, 1993 (Jun. 15, 1993), pp. 5618-5622, XP002676370—ISSN 0027-8424, DOI: 10.1073/PNAS.9012. 5618.
Gurevich et al.: "Custom-designed proteins as novel therapeutic tools? The case of arrestins", Expert Rev. Mol. Med.; 12; e13; 2010; DOI:10.1017/S1462399410001444.
Gurevich et al.: Structural Determinats of Arrestin Functions, Progress in Molecular Biology and Translational Science, vol. 118, 2013, ISSN 1877-1173,

* cited by examiner

FIG 1

Scanning mutagenesis on arrestin

```
          10         20         30         40         50         60         70
M̲I̲K̲KANKPAPNH VIFKKISRDK SVTIYLGKRD YIDHVERVEP VDGVVLVDPE LVKGKRVYVS LTCAFRYGQE
          80         90        100        110        120        130        140
DIDVMGLSFR RDLYFSQVQV FPPVGASGAT TRLQESLIKK LGANTYPFLL TFPDYLPCSV MLQPAPQDVG
         150        160        170        180        190        200        210
KSCGVDFEIK AFATHSTDVE EDKIPKKSSV RLLIRKVQHA PRDMGPQPRA EASWQFFMSD KPLRLAVSLS
         220        230        240        250        260        270        280
KEIYYHGEPI PVTVAVTNST EKTVKKIKVL VEQVTNVVLY SSSYYIKTVA AEEAQEKVPP NSSLTKTLTL
         290        300        310        320        330        340        350
VPILANNRER RGIALDGKIK HEDTNLASST IIKEGIDKTV MGILVSYQIK VKLTVSGLLG ELTSSEVATE
         360        370        380        390        400
VPFRLMHPQP EDPDTAKESF QDENFVFEEF ARQNLKDAGE YKEEKTDQEA AMDE
```

Each residue was mutated
individually to alanine/glycine

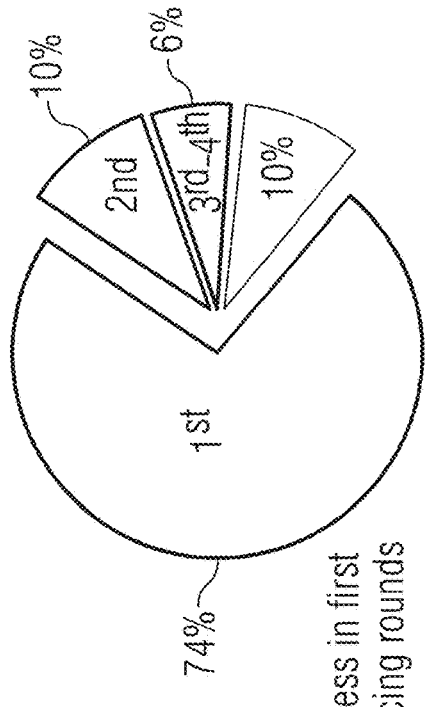

74% 1st
10% 2nd
6% 3rd
10% 4th

87% success in first
3 sequencing rounds

FIGURE 9

```
SP|sp|P08168|ARRS_BOVIN|ARRS_BOVIN   ---MKANKPAPNHVFKKISRDKSVTIYLGKRDYIDHVERVEPVDGVVLVDPELVKGKR  56
SP|sp|P10523|ARRS_HUMAN|ARRS_HUMAN   MAASGKTSKSEPNHVFKKISRDKSVTIYLGNRDYIDHVSQVQPVDGVVLVDPDLVKGKK  60
SP|sp|P49407|ARRB1_HUMAN|ARRB1_HUMAN ------MGDKGTRVFKKASPNGKLTVYLGKRDFVDHIDLVDPVDGVVLVDPEYLKERR  52
SP|sp|P32121|ARRB2_HUMAN|ARRB2_HUMAN ------MGEKPGTRVFKKSSPNCKLTVYLGKRDFVDHLDKVDPVDGVVLVDPDYLKDRK  53
SP|sp|P36575|ARRC_HUMAN|ARRC_HUMAN   ---------MSKVFKKTSSNGKLSIYLGKRDFVDHVDTVEPIDGVVLVDPEYLKCRK  48
                                              *    ***..**.**. *.*.********..*..

SP|sp|P08168|ARRS_BOVIN|ARRS_BOVIN   VYVSLTCAFRYGQEDIDVMGLSFRRDLYFSQVQVFPPVG--ASGATTRLQESLIKKLGAN 114
SP|sp|P10523|ARRS_HUMAN|ARRS_HUMAN   VYVTLTCAFRYGQEDIDVIGLTFRRDLYFSRVQVYPPVG--AASTPTKLQESLLKKLGSN 118
SP|sp|P49407|ARRB1_HUMAN|ARRB1_HUMAN VYVTLTCAFRYGREDLDVLGLTFRKDLFVANVQSFPPAP-EDKKPLTRLQERLIKKLGEH 111
SP|sp|P32121|ARRB2_HUMAN|ARRB2_HUMAN VFVTLTCAFRYGREDLDVLGLSFRKDLFIATYQAFPPVP-NPPRPPTRLQDRLLRKLGQH 112
SP|sp|P36575|ARRC_HUMAN|ARRC_HUMAN   LFVMLTCAFRYGRDDLEVIGLTFRKDLYVQTLQVVPAESSSPQGPLTVLQERLLHKLGDN 108
                                     ..: ******* *.. * .**.**:**:. .   : ...          *:.:*.**:

SP|sp|P08168|ARRS_BOVIN|ARRS_BOVIN   TYPFLLTFPDYLPCSVMLQPAPQDVGKSCGVDFEIKAFATHSTDVEEDKIPKKSSVRLLI 174
SP|sp|P10523|ARRS_HUMAN|ARRS_HUMAN   TYPFLLTFPDYLPCSVMLQPAPQDSGKSCGVDFEVKAFATDSTDAEEDKIPKKSSVRLLI 178
SP|sp|P49407|ARRB1_HUMAN|ARRB1_HUMAN AYPFTFEIPPNLPCSVTLQPGPEDTGKACGVDYEVKAFCAEN---LEEKIHKRNSVRLVI 168
SP|sp|P32121|ARRB2_HUMAN|ARRB2_HUMAN AHPFFFTIPQNLPCSVTLQPGPEDTGKACGVDFEIRAFCAKS---LEEKSHKRNSVRLVI 169
SP|sp|P36575|ARRC_HUMAN|ARRC_HUMAN   AYPFTLQMVTNLPCSVTLQPGEDAGKPCGIDFEVKSFCAEN---PEETVSKRDYVRLVV 165
                                     :*** .  .********  ** *   .*.***:*::* :      :      .***::

SP|sp|P08168|ARRS_BOVIN|ARRS_BOVIN   RKVQHAPRDMGPQPRAEASWQFFMSDKPLRLAVSLSKEIYYHGEPIPVTAVTNSTEKTV 234
SP|sp|P10523|ARRS_HUMAN|ARRS_HUMAN   RKVQHAPLEMGPQPRAEAAWQFFMSDKPLHLAVSLNKEIYFHGEPIPVTVTVTNNTEKTV 238
SP|sp|P49407|ARRB1_HUMAN|ARRB1_HUMAN RKVQYAPERPGPQPTAETTRQFLMSDKPLHLEASLDKEIYYHGEPISVNVHVTNNSTKTV 228
SP|sp|P32121|ARRB2_HUMAN|ARRB2_HUMAN RKVQFAPEKPGPQPSAETTRHFLMSDRSLHLEASLDKELYYHGEPLNVNVHVTNNSTKTV 229
SP|sp|P36575|ARRC_HUMAN|ARRC_HUMAN   RKVQFAPPEAGPGPSAQTIRRFLLSAQPLQLQAWMDREVHYHGEPISVNVSINNCTNKVI 225
                                     ****.**   ****:*:.   :*:*.: *:* . :.:*::*****:.*.*  *. *.*

SP|sp|P08168|ARRS_BOVIN|ARRS_BOVIN   KKIKVLVEQVTNVVLYSSDYYIKTVAAEEAQEKVPPNSSLTKTLTLVPLLANNRERRGIA 294
SP|sp|P10523|ARRS_HUMAN|ARRS_HUMAN   KKIKAFVEQVANVVLYSSDYYVKPVAMEEAQEKVPPNSTLTKTLTLLPLLANNRERRGIA 298
SP|sp|P49407|ARRB1_HUMAN|ARRB1_HUMAN KKIKISVRQYADICLFNTAQYKCPVAMEEADDTVAPSSTFCKVYTLTPFLANNREKRGLA 288
SP|sp|P32121|ARRB2_HUMAN|ARRB2_HUMAN KKIKVSVRQYADICLFNTAQYKCPVAQLEQDDQVSPSSTFCKVYTITPLLSDNREKRGLA 289
SP|sp|P36575|ARRC_HUMAN|ARRC_HUMAN   KKIKISVDQITDWLYSLDKYTKTVFIQEFTETVAANSSFSQSFAVTPILAASCQKRGLA 285
                                     ****  *.*  :  :.  .* * *  :*     *  .*::    .: .:: .*::**:*

SP|sp|P08168|ARRS_BOVIN|ARRS_BOVIN   LDGKIKHEDTNLASSTIIKEGIDKTVMGILVSYQIKVKLTV--SGLLGELTSSEVATEVP 352
SP|sp|P10523|ARRS_HUMAN|ARRS_HUMAN   LDGKIKHEDTNLASSTIIKEGIDRTVLGILVSYQIKVKLTV--SGFLGELTSSEVATEVP 356
SP|sp|P49407|ARRB1_HUMAN|ARRB1_HUMAN LDGKLKHEDTNLASSTLLREGANREILGIIVSYKVKVKLVVSRGGLLGDLASSDVAVELP 348
SP|sp|P32121|ARRB2_HUMAN|ARRB2_HUMAN LDGKLKHEDTNLASSTIVKEGANKEVLGILVSYRVKVKLVVSRGG---------DVSVELP 341
SP|sp|P36575|ARRC_HUMAN|ARRC_HUMAN   LDGKLKHEDTNLASSTIIRPGMDKELLGILVSYKVRVNLMVSCGGILGDLTASDVGVELP 345
                                     ****:**********:: .*  : :: **:***::.*.*.*                *

SP|sp|P08168|ARRS_BOVIN|ARRS_BOVIN   FRLMHPQPEDPDTAK---------------ESFQDENFVFEEFARQNLKDAGE 390
SP|sp|P10523|ARRS_HUMAN|ARRS_HUMAN   FRLMHPQPEDP-AK----------------ESYQDANLVFEEFARHNLKDAGE 392
SP|sp|P49407|ARRB1_HUMAN|ARRB1_HUMAN FTLMHPKPKEEPP---HREVPENETPVDTNLIELDTN--DDDIVFEDFARQRLKGMKD 401
SP|sp|P32121|ARRB2_HUMAN|ARRB2_HUMAN FVLMHPKPHDHIPLPRPQSAAPETDVPVDTNLIEFDTNYATDDDIVFEDFARLRLKGMKD 401
SP|sp|P36575|ARRC_HUMAN|ARRC_HUMAN   LVLIHPKPSHEAAS-----------------SEDIVEEFTRKGEEESQK 378
                                     : *:**:* :                          .   :.

SP|sp|P08168|ARRS_BOVIN|ARRS_BOVIN   YKEEKTDQEAAMDE-- 404
SP|sp|P10523|ARRS_HUMAN|ARRS_HUMAN   AEEGKRDKNDVDE--- 405
SP|sp|P49407|ARRB1_HUMAN|ARRB1_HUMAN DKEEEEDGTGSPQLNNR 418
SP|sp|P32121|ARRB2_HUMAN|ARRB2_HUMAN DDYDDQLC--------- 409
SP|sp|P36575|ARRC_HUMAN|ARRC_HUMAN   AVEA-EGDEGS------ 388
```

METHOD FOR DETERMINING MUTATEABLE LIGAND-GPCR BINDING AT SINGLE AMINO ACID RESOLUTION AND PAIRS OF MUTATED LIGAND AND GPCR

REFERENCE TO AN ELECTRONIC SEQUENCE LISTING

The contents of the electronic sequence listing (01920067US1seqlist.txt; Size: 17,905 bytes; and Date of Creation Jul. 12, 2018) is herein incorporated by reference in its entirety.

BACKGROUND OF THE INVENTION

Field of the Invention

The present invention relates to a method to determine the binding ability of a mutatable ligand to a G-protein coupled receptor (GPCR). Further, the present invention relates to specific mutant ligands as well as specific pairs of mutant ligands and GPCRs as well as specific use of said mutant ligands and/or pairs of mutant ligands and GPCRs.

G protein coupled receptors (GPCRs) are a large class of seven transmembrane domain receptors that transduce signals from outside the cells when bound to an appropriate ligand. The GPCRs have a myriad of functions, being involved in sensory perceptions, such as odor and vision, responding to pheromones, hormones and neurotransmitters, where the ligands greatly vary in nature and size. The GPCRs can affect behavior and mood, the immune system, the sympathetic and parasympathetic nervous system, cell density sensing and there may be additional physiological activities that involve GPCRs in their pathway. The GPCRs are associated with a number of diseases and have been an active target of pharmaceutical companies.

As mentioned above, GPCRs are involved in a wide variety of physiological processes. Some examples of their physiological roles include:
1. The visual sense: the opsins use a photoisomerization reaction to translate electromagnetic radiation into cellular signals. Rhodopsin, for example, uses the conversion of 11-cis-retinal to all-trans-retinal for this purpose
2. The sense of smell: receptors of the olfactory epithelium bind odorants (olfactory receptors) and pheromones (vomeronasal receptors)
3. Behavioral and mood regulation: receptors in the mammalian brain bind several different neurotransmitters, including serotonin, dopamine, Gamma aminobutyric acid, and glutamate
4. Regulation of immune system activity and inflammation: chemokine receptors bind ligands that mediate intercellular communication between cells of the immune system; receptors such as histamine receptors bind inflammatory mediators and engage target cell types in the inflammatory response
5. Autonomic nervous system transmission: both the sympathetic and parasympathetic nervous systems are regulated by GPCR pathways, responsible for control of many automatic functions of the body such as blood pressure, heart rate, and digestive processes
6. Cell density sensing: A novel GPCR role in regulating cell density sensing.
7. Homeostasis modulation (e.g., water balance)
8. Involved in growth and metastasis of some types of tumors.

GPCRs are activated by an external signal resulting in a conformational change. It appears that once the receptor becomes bound it activates the G protein, which G protein is bound to ATP. The G protein is a trimer, which upon activation converts GTP (guanosine triphosphate) to GDP (guanosine diphosphate). Active GPCRs are phosphorylated by protein-coupled receptor kinases. In many cases upon phosphorylation, the phosphorylated receptor becomes linked to arrestin. The binding to arrestin may result in translocation of the GPCR or other outcome.

In response to a stimulus, GPCRs activate heterotrimeric G proteins. In order to turn off this response, or adapt to a persistent stimulus, active receptors need to be desensitized. The first step is phosphorylation by a class of serine/threonin kinases called G protein coupled receptor kinases (GRKs). GRK phosphorylation specifically prepares the activated receptor for arrestin binding. Arrestin binding to the receptor blocks further G protein-mediated signaling and targets receptors for internalization, and redirects signaling to alternative G protein-independent pathways, such as β-arrestin signaling. In addition to GPCRs, arrestins bind to other classes of cell surface receptors and a variety of other signaling proteins.

Arrestins are elongated molecules, in which several intramolecular interactions hold the relative orientation of the two domains. In unstimulated cell arrestins are localized in the cytoplasm in this basal "inactive" conformation. Active phosphorylated GPCRs recruit arrestin to the plasma membrane. Receptor binding induces a global conformational change that involves the movement of the two arrestin domains and the release of its C-terminal tail that contains clathrin and AP2 binding sites. Increased accessibility of these sites in receptor-bound arrestin targets the arrestin-receptor complex to the coated pit. Arrestins also bind microtubules (part of the cellular "skeleton"), where they assume yet another conformation, different from both free and receptor-bound form. Microtubule-bound arrestins recruit certain proteins to the cytoskeleton, which affects their activity and/or redirects it to microtubule-associated proteins. Arrestins shuttle between the cell nucleus and the cytoplasm. Their nuclear functions are currently under intense investigation and it was shown that all four mammalian arrestin subtypes remove some of their partners, such as protein kinase JNK3 or the ubiquitin ligase Mdm2, from the nucleus. Arrestins also modify gene expression by enhancing transcription of certain genes.

Mammals express four arrestin subtypes and each arrestin subtype is known by multiple aliases. The systematic arrestin name (1-4) plus the most widely used aliases for each arrestin subtype are listed in bold below:

Arrestin-1 was originally identified as the S-antigen (SAG) causing uveitis (autoimmune eye disease), then independently described as a 48 kDa protein that binds light-activated phosphorylated rhodopsin before it became clear that both are one and the same. It was later renamed visual arrestin, but when another cone-specific visual subtype was cloned the term rod arrestin was coined. This also turned out to be a misnomer: arrestin-1 expresses at comparable very high levels in both rod and cone photoreceptor cells.

Arrestin-2 was the first non-visual arrestin cloned. It was first named β-arrestin simply because between two GPCRs available in purified form at the time, rhodopsin and β₂-adrenergic receptor, it showed preference for the latter.

Arrestin 3: The second non-visual arrestin cloned was first termed β-arrestin-2 (retroactively changing the name of β-arrestin into β-arrestin-1), even though by that time it was clear that non-visual arrestins interact with hundreds of different GPCRs, not just with $β_2$-adrenergic receptor. Systematic names, arrestin-2 and arrestin-3, respectively, were proposed soon after that.

Arrestin-4 was cloned by two groups and termed cone arrestin, after photoreceptor type that expresses it, and X-arrestin, after the chromosome where its gene resides. In the HUGO database its gene is called arrestin-3.

Arrestins block GPCR coupling to G proteins via two mechanisms. First, arrestin binding to the cytoplasmic tip of the receptor occludes the binding site for the heterotrimeric G protein, preventing its activation (desensitization). Second, arrestins link the receptor to elements of the internalization machinery, clathrin and clathrin adaptor AP2 (C-terminal tail), which promotes receptor internalization via the coated pits and subsequent transport to internal compartments, called endosome. Subsequently, the receptor could be either directed to degradation compartments (lysosomes) or recycled back to the plasma membrane where it can once more act as a signal. The strength of arrestin-receptor interaction plays a role in this choice: tighter complexes tend to increase the probability of receptor degradation, whereas more transient complexes favor recycling, although this "rule" is far from absolute.

Therefore, arrestins function as adapter proteins that facilitate desensitization, internalization and signaling of G protein-coupled receptors (GPCRs). Quenching of G protein signaling via arrestins is best understood in the visual system where arrestin-1 quenches phototransduction via its ability to bind to the phosphorylated, light-activated form of the visual photoreceptor rhodopsin.

The binding ability of ligands to their respective GPCR, such as the arrestin-rhodopsin complex, opens a broad field of drug discovery and drug screening in order to diagnose and treat diseases in the field of the GPCR moderated exocytotic or endocytotic biochemical processes. The international patent application WO 2008/114020 A2 discloses a method for selecting a GPCR with increased stability. Said method comprises a) providing one or more mutants of a parent GPCR, b) selecting a ligand, the ligand being one which binds to the parent GPCR when the GPCR is residing in a particular conformation, c) determining whether the or each mutant GPCR has increased stability with respect to binding the selected ligand compared to the stability of the parent GPCR with respect to binding that ligand, and d) selecting those mutants that have an increased stability compared to the parent GPCR with respect to binding the selected ligand. Mutants of β-adrenergic receptor, adenosine receptor and neurotensin receptor are also disclosed in this application.

Unfortunately, the number of mutants of the GPCRs which represent the same biochemical behavior as the parent GPCR are limited. Further, mutant GPCRs are rather difficult to be synthesized and therefore the binding assays are rather expensive due to the expensive mutant GPCRs.

BRIEF SUMMARY OF THE INVENTION

It is therefore an objective of the present invention to provide a method for identifying the binding ability of GPCRs to ligand at lower cost and with a broader spectrum of ligand-GPCR pairs. Further, it is an objective of the present invention to stabilize the binding of the ligand and the GPCR by suitable ligands and/or suitable ligand/GPCR pairs.

This objective is achieved according to the present invention by a method for determining the binding ability of a G-protein coupled receptor, hereinafter referred to as GPCR, and a mutatable ligand, said method comprising the steps of:
a) providing a well microtiter plate having the wells disposed in a matrix having a first number of rows and a second number of columns;
b) providing a GPCR, such as rhodopsin, in each of said wells;
c) providing a number of mutants of the parent ligand, wherein the parent ligand being one that binds to the GPCR when the GPCR is residing in a particular conformation;
d) bringing the mutants of the parent ligand in the wells into contact with the GPCR under conditions where the parent ligand would couple to the GPCR; and
e) determining for each mutant whether the mutant ligand has a weaker or stronger binding ability as compared to the standard binding ability of the parent ligand and the GPCR by determining the amount of coupled mutant-GPCR complex in said wells.

The present method therefore offers the opportunity to simultaneously scan the binding ability of the mutants of a parent ligand within the same set-up conditions of the assay for a number of mutants wherein the mutagenesis on the ligand can be executed at residue resolution due to the simpler organic structure of the mutatable ligand as compared to the structure of the GPCR that has been mutated for example in the WO 2008/114020 A2. Further, the combination of mutants allows the modification of binding affinity and stability of the GPCR-ligand complex for diagnostic purposes, pharmacological intervention or drug discovery.

In order provide conditions that deliver a certain gradient of the reaction conditions in the wells, a preferred embodiment of the present inventions is present where for the wells of each row or each column the same mutant is used and wherein the reaction condition in the well, such as salt concentration or solvent agent, changes from well to well in said row or in said column.

For providing the advantageous and comparable reaction conditions in the wells, the reaction condition can be kept constant in those wells belonging to the same row or to the same column.

In order to provide a reference value of the binding of the parent ligand and the GPCR to the assay, the parent ligand may be added to all wells belonging to the same row or the same column of the well microtiter plate. With other words, the conditions under which the mutants are tested are also applied to the parent ligand-GPCR pair which enhances the scalability of the results for the mutants simultaneously tested. Any impact on the reaction conditions that might differ from one well microtiter plate assay to the other, can therefore be eliminated due to the reference value identified for the parent ligand-GPCR-pair.

Advantageously, the mutants are provided in solubilized form that enables rather simple assay conditions for the investigation on the binding ability of a specific mutant ligand to the GPCR.

In a further preferred embodiment of the present invention, the parent ligand can be from the agonist class of ligands and the particular conformation is an agonist conformation, or the parent ligand is from the antagonist class of ligands and the particular conformation is an antagonist conformation. Preferably, the parent ligand is any one of a full agonist, a partial agonist, an inverse agonist, an antagonist, or the parent ligand is from the inverse agonist class of ligands and the particular conformation is an inverse agonist conformation. Therefore, these ligands guarantee the application of the assay trials with respect to the binding ability on the interesting spectrum of in-vivo biochemical reactions that are controlled/influenced by the GPCR and its binding stabilization to the mutant ligands in question.

In a further preferred embodiment of the present invention, the parent ligand is a polypeptide which binds to the GPCR. Preferably, the polypeptide is any of an antibody, an ankyrin, a G protein, an RGS protein, an arrestin, a GPCR kinase, a receptor tyrosine kinase, a RAMP, a NSF, a GPCR, an NMDA receptor subunit NR1 or NR2a, a calcyon, a fibronectin domain framework, or a fragment or derivative thereof that binds to the GPCR.

In a further preferred embodiment of the present invention the mutants of the parent ligand are provided in a form that one of more mutated amino acid residues are replacing the parent amino acid residue. Preferably, a parent amino acid residue can be mutated individually to alanine/glycine.

Excellent results on the binding ability can be achieved when the parent ligand is one of arrestin 1, arrestin 2, arrestin 3 and arrestin 4. Preferably, mutants of the parent ligand having a higher binding affinity to the GPCR than the parent mutant are candidates for drug discovery.

With respect to the pair of a mutant ligand and a GPCR, a solution for the objective mentioned above is achieved by a pair of a mutant ligand and a GPCR wherein the binding stability of said pair is higher as compared to the pair consisting of the parent ligand and the GPCR, preferably identified according to the method of the invention. Accordingly, an alternative solution for a pair of mutant ligand and a GPCR is achieved by a pair of a mutant ligand and a GPCR wherein the binding stability of said pair is lower as compared to the pair consisting of the parent ligand and the GPCR, preferably identified according to the method of the invention.

Further, the objective is achieved according to the present invention with respect to the ligand by a mutant ligand of the parent ligand of the arrestin type having a higher binding stability with a GPCR than the pair of the parent ligand and the GPCR, preferably identified according to the method of the invention. Alternatively, this objective is achieved according to the present invention by a mutant ligand of the parent ligand of the arrestin type having a lower binding stability with a GPCR than the pair of the parent ligand and the GPCR, preferably identified according to the method of the invention.

Further aspect of the present invention is achieved by the use of the pair according to claim 11 or 12 or the mutant ligand of claim 13 or 14 in a drug screening using complementation assay with mutant ligands optimized for either higher or lower affinity to the GPCR as compared to the binding affinity of the parent ligand and the GPCR.

BRIEF DESCRIPTION OF THE SEVERAL VIEWS OF THE DRAWING

Preferred embodiments of the present invention are hereinafter described in more detail with reference to the following drawings which depict in:

FIG. 1 an overview of the scanning mutagenesis on arrestin;

FIG. 9 schematically the transfer of mutations to other arrestins.

DESCRIPTION OF THE INVENTION

Table 1 (at the end of the specification) shows the relative binding affinities for mutants covering the complete sequence of the GPCR ligand arrestin-1. Herein, each amino acid position in the arrestin has been mutated to alanine (A) or glycine (G).

FIG. 1 shows the amino acid sequence of bovine arrestin-1 depicted in SEQ ID NO:5. The scanning mutagenesis on arrestin was executed by known sequencing technologies in order to mutate each residue individually to alanine (A) or glycine (G). During the first sequencing round 74% of the 403 mutant ligands have been successfully generated. Complete coverage has been achieved after further mutagenesis and sequencing rounds.

Figure 2:
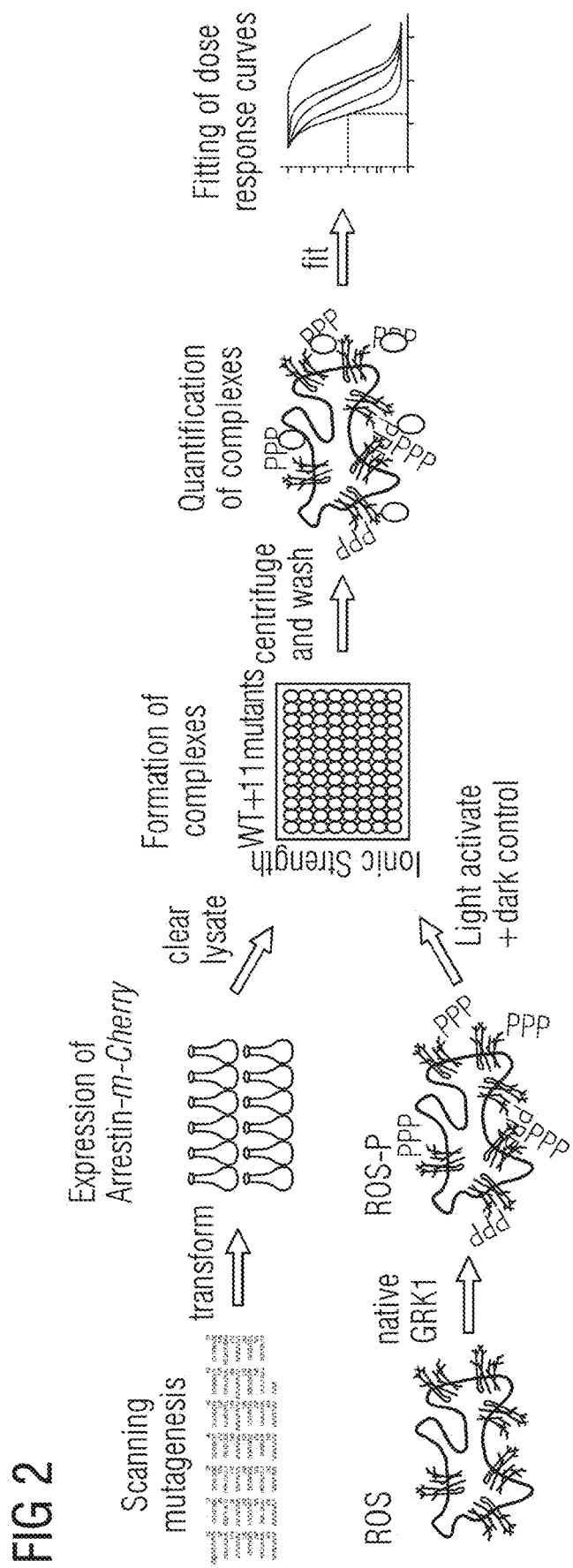
FIG. 2 schematically an binding assay using arrestin-mCherry and rhodopsin in native rod outer segment (ROS) membranes.

As schematically illustrated in FIG. 2, the mutants of the arrestin-1 that have been obtained by scanning mutagenesis are transformed into *Escherichia coli* (*E. coli*). The relative expression level of each mutant with respect to the wild type (parent ligand) was determined using fluorescence of a C-terminal mCherry fusion to arrestin. For complex formation arrestin is combined with rhodopsin in rod outer segment (ROS) membranes that had been phosphorylated with native rhodopsin kinase (GRK1). To minimize the effect of variations in the expression of different arrestin mutants the assay contained 1.25 µM rhodopsin, far in excess of the 5-50 nM apparent binding affinity of arrestin-1. Consequently, no correlation has been observed between the amounts of functionally expressed arrestin-1 and the ability of a mutant to bind rhodopsin under increasing ionic strength measured as described below.

Although, the present examples will now discuss in more detail the complex (pair) of arrestin as parent ligand and rhodopsin as GPCR, the method according to the present invention is open to scan any arbitrary pair of parent ligand and GPCR. In particular, the use of the well microtiter plate offers a brought range of scanning experiments which can be established simultaneously under reaction conditions that are equal for all mutated ligands.

In more detail, FIG. 2 shows the direct binding assay of arrestin-mCherry and rhodopsin in native ROS membranes. Plasmids containing arrestin mutated by scanning mutagenesis were transformed into *E. coli*. The relative expression level of each mutant with respect to the wild type was determined using fluorescence of a C-terminal mCherry fusion to arrestin. For complex formation arrestin is combined with rhodopsin in ROS membranes that had been phosphorylated with native rhodopsin kinase (GRK1). For comparison of relative binding in the present example, each time 11 arrestin mutants and wild-type arrestin as control were combined in a 96-well microtiter plate and probed for binding to to light-activated rhodopsin in eight different salt concentrations. For dark-adapted rhodopsin, only single point measurements were conducted for each mutant. After centrifugation and washing steps, the amount of bound arrestin was quantified using fluorescence of the mCherry fusion protein. The resulting data were fitted to sigmoidal dose-response curves with variable slope to extract the IC50 values and 95% confidence intervals as listed in Table 1.

A library of 403 arrestin mutants has been screened for their $IC_{50}$ values. All measurements were performed in the frame of fluorescence quantification of arrestin-mCherry fusion proteins. To find mutant combinations that would increase binding, 23 of 24 mutants with the highest $IC_{50}$ values measured were selected, ranging from 1.14 M for G297A till 0.56 M for R291A, from the arrestin-1 mutant library. They were combined with the strongest binding mutation F375A ($IC_{50}$=1.32±0.31 M). Further, 15 mutants were selected with significantly higher $IC_{50}$ values than WT (wild type). As control 10 mutants were chosen with $IC_{50}$ values similar to WT (within the standard deviation of WT measurements) and 2 mutants with significantly lower $IC_{50}$ values than WT as well as 3 mutants that showed a weak signal (I24A, V57A, and I149A) due to low functional expression levels. Altogether, 53 double mutants have been constructed. The screening procedure for $IC_{50}$ values was then extended additionally to the one previously employed with a second range of assayed sodium chloride concentrations to be able to fit binding data of mutants with high $IC_{50}$ values with adequate accuracy. Each combined mutant was subjected to both sodium chloride screening ranges to derive $IC_{50}$ values (FIG. 4).

Figure 4:
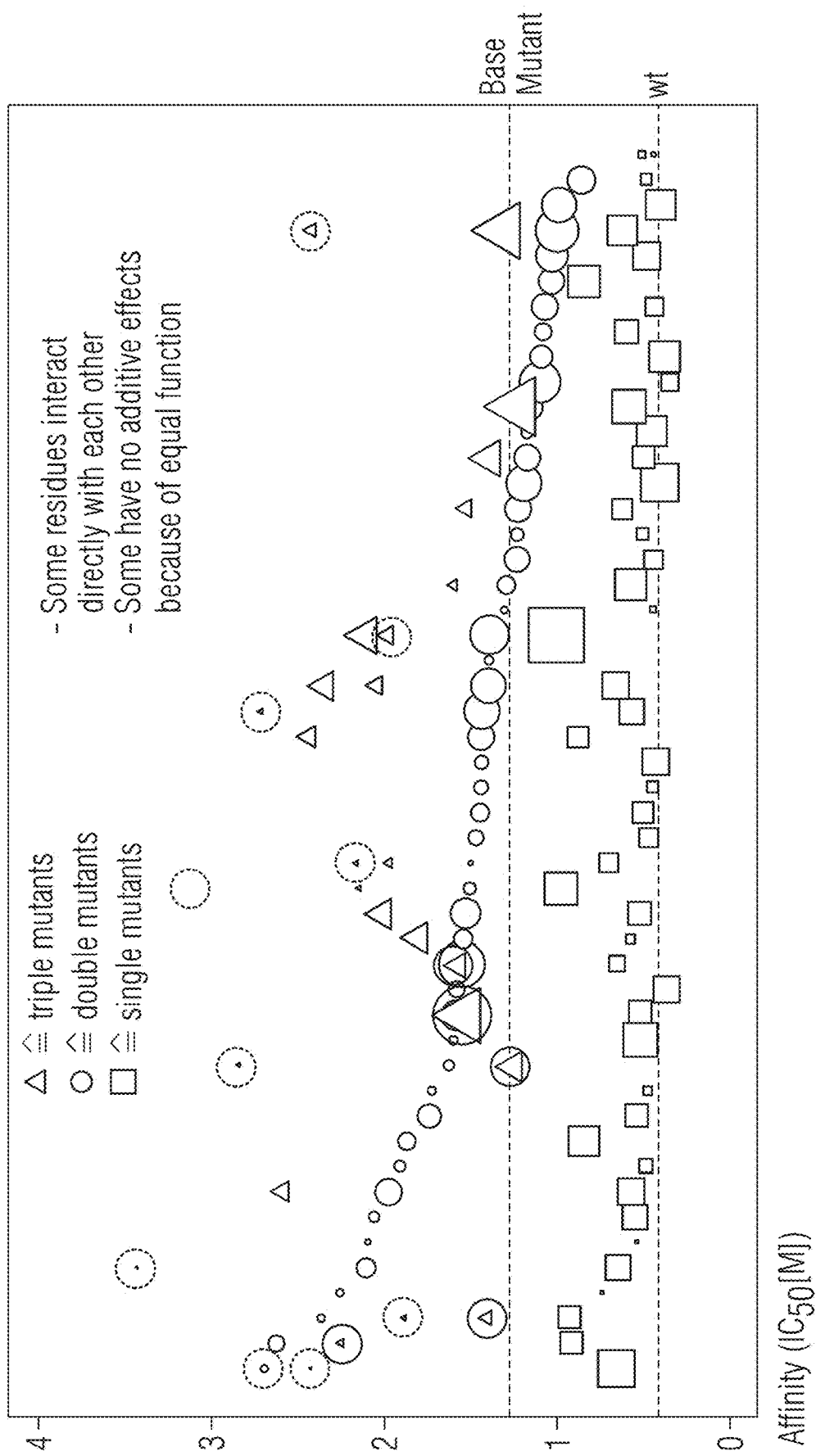
FIG. 4 an overview on the combination of mutations to create an arrestin "Super Binder"

FIG. 4 shows the half-maximal inhibitory concentration ($IC_{50}$) values of sodium chloride for formation of complexes composed of mutant arrestin-1 and phosphorylated activated rhodopsin. Double mutants (circles) are sorted by decreasing $IC_{50}$ value (from left to right) and are composed of F375A+X, where the single mutant X is shown underneath and named on the x-axis. Triple mutants (triangles) are composed of either F375A+A307G+X or F375A+T304A+X, while quadruple mutants are combined like F375A+T304A+E341A+X or like F375A+T304A+F380A+X. The size of the shape encodes the functional expression level of regarding mutant and is scaled in relation to the arrestin-1 wild type functional expression level (legend). The functional expression level tells how much of arrestin protein, functional in terms of rhodopsin binding, was expressed and pulled down for regarding mutant in relation to wild type arrestin-mCherry construct at 100 mM NaCl. In case of combined mutants with elevated IC50, the reference point was mutant F375A at 492 mM NaCl.

The $IC_{50}$ values could be derived for 49 out of 53 double mutants, 4 double mutants exposed signal intensities below detection limit. About two thirds, exactly 33 of 49 mutants, exhibited $IC_{50}$ values similar to F375A (within the standard deviation of the $IC_{50}$ value derived in 23 independent measurements for F375A, see above). A sum of 12 mutants had significantly higher $IC_{50}$ values than F375A and 4 double mutants significantly lower values. Another series of mutations has been added on top of double mutant A307G+F375A, which was leading the screen with the highest $IC_{50}$ value observed (2.83 M), or on top of mutant T304A+F375A, which was with an $IC_{50}$ value of 1.51 M under the 12 best-binding mutants. Of 38 constructed triple mutants $IC_{50}$ values for 35 mutants could be determined and those were ranging from 3.52 to 1.01 M. Although triple mutants containing A307G bound in very high salt concentrations to light-activated phosphorylated rhodopsin (R*-P), quantitatively the amounts of formed complexes were low. Thus triple mutants E341A+T304+F375A and F380A+T304A+F375A were chosen with $IC_{50}$ values of 2.75 M and 2.09 M, respectively, to design 15 quadruple mutants. For quadruple mutants, $IC_{50}$ values from 2.95 M to 1.37 M have been obtained. The two quadruple mutants R171A+E341A+T304A+F375A and D303A+E341A+T304A+F375A reached $IC_{50}$ values amounting to 720% and 710% of the WT value (0.41±0.05 M) (FIG. 4 and Table 2). Conclusively, it was possible to increase complex stability more than 7 times under the pressure of high ionic strength by selection and combination of single mutants to quadruple mutants.

As a short example, for comparison of relative binding, 11 arrestin mutants and WT arrestin as control were combined in a 96 well microtiter plate and probed for binding to dark and light activated rhodopsin in 8 different salt concentrations (100 mM to 2.4 M). After centrifugation and washing steps the amount of bound arrestin has been quantified using fluorescence of the mCherry fusion protein. The resulting data were fitted to sigmoidal dose-response curves with variable slope to extract half maximal inhibitory concentration ($IC_{50}$) values and 95% confidence intervals listed in table 1 (at the end of the specification). A selection of strong and weak binding mutations discussed in the main text have been measured several times to increase accuracy of the determined $IC_{50}$ values. The variation of $IC_{50}$ values for WT arrestin was 0.41±0.04 M from 59 independent experiments in agreement with previous reports using radiolabeled arrestin-1. Among the 25 best binding mutations, 13 affected polar residues including 10 residues that are charged under physiological conditions. Similarly, 10 of the worst 25 binding mutations affected polar residues including 4 charged residues. This even distribution between polar and hydrophobic residues demonstrates that the assay is not biased even though increasing ionic strength predominately affects hydrophilic interactions. This is in agreement with the idea that arrestin binding to rhodopsin involves a multitude of hydrophilic and hydrophobic interactions, as well as specific conformational changes and is not dominated by a few charged interactions.

Figure 3:
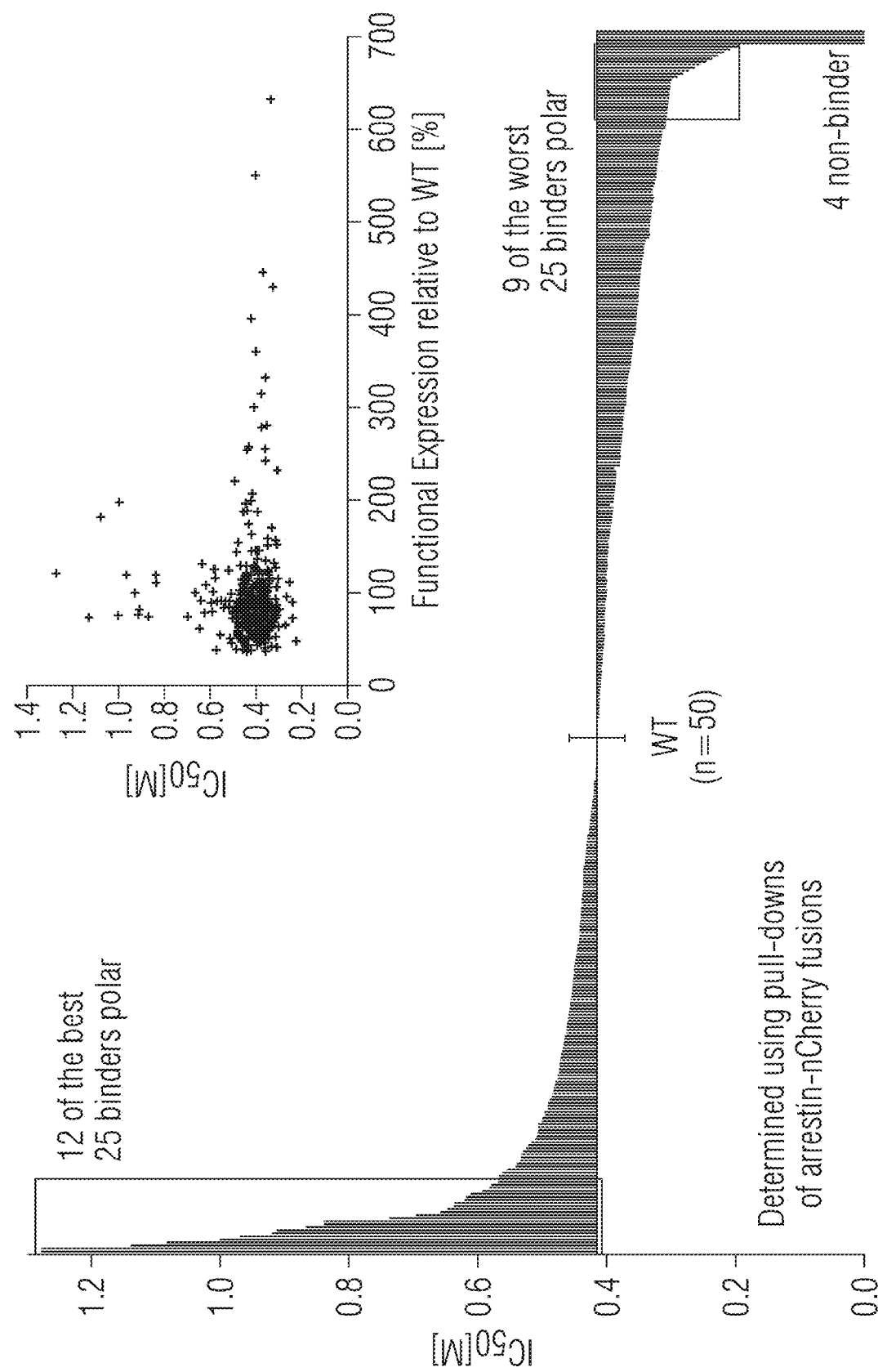
FIG. 3 an overview on the course of the half maximal inhibitory concentration $IC_{50}$ of the mutant ligands of arrestin.

FIG. 3 provides an overview on the course of the half maximal inhibitory concentrations ($IC_{50}$ values) of all single mutant ligands of arrestin. The investigation involved the binding ability of all 403 arrestin mutants listed in table 1. Using the pull downs of an arrestin-mCherry fusion protein, the analysis comprised the comparison of the rhodopsin binding of all 403 mutants covering the complete arrestin sequence. This information provides a functional $4^{th}$ dimension to the crystal structures of inactive, preactivated and active arrestins. The resulting single amino acid resolution functional maps reveal a series of critical interactions in the polar core and along the C-tail of arrestin that are interrupted during arrestin activation.

Figure 7:
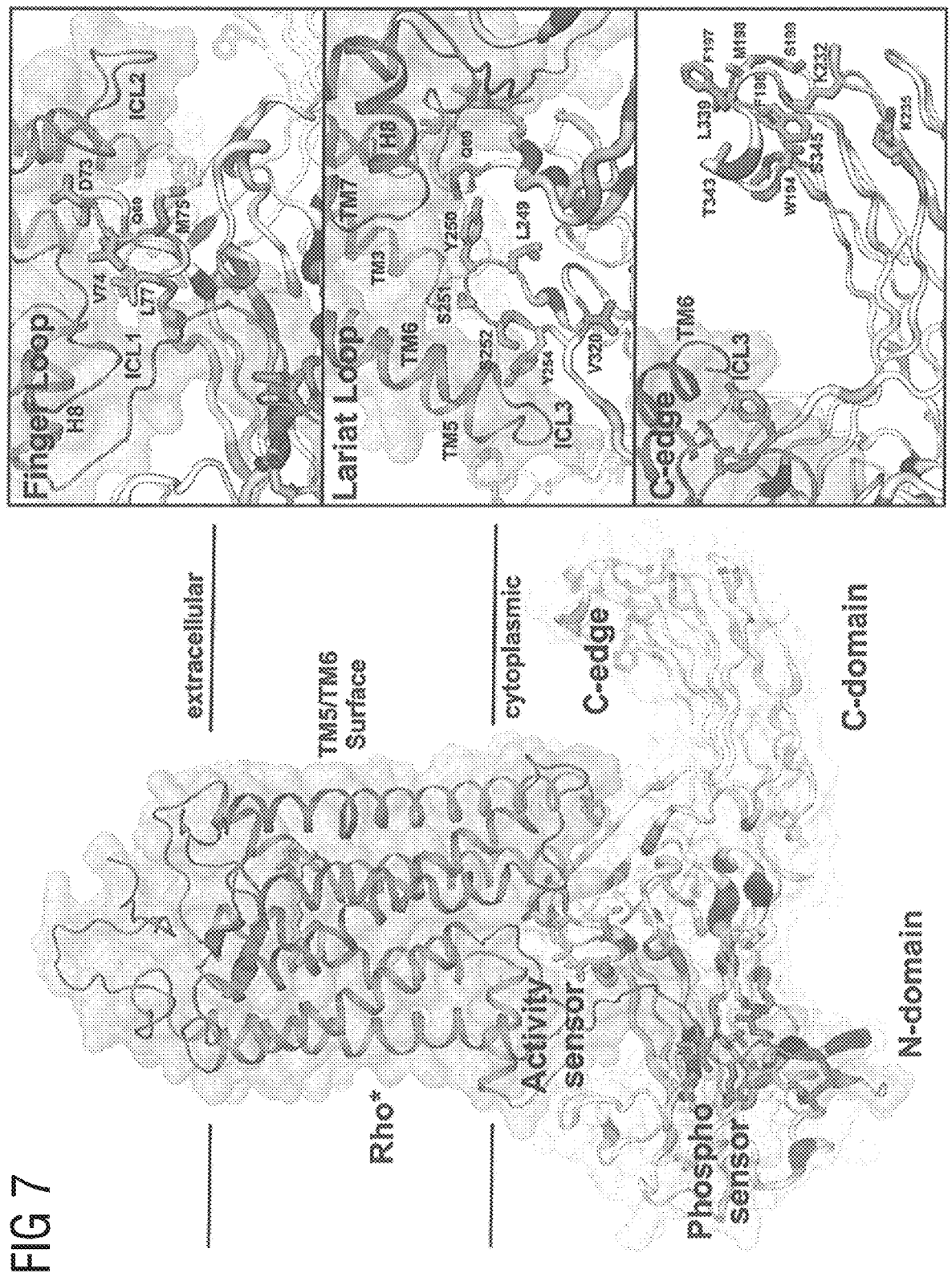
FIG. 7 schematically the model of the arrestin-rhodopsing complex.

The data further reveals several patches of amino acids that strongly reduce binding and act as direct binding interfaces to rhodopsin. This information in combination with computational molecular docking of active arrestin and light-activated rhodopsin allow to develop a model of the arrestin-rhodopsin complex as shown in FIG. 7. FIG. 4 shows the combination of mutations of the arrestin-1 ligand in terms of their binding affinity to rhodopsin. Rectangular symbols represent the mutant ligands which have just one mutated amino acid position; the circular symbols represent the assays with mutant ligands having two mutated amino acid positions, and the triangular symbol represent assays with mutant ligands comprising tree mutated amino acid positions. Rhombic symbols represent quadruple mutant ligands of arrestin-1.

Figure 5:
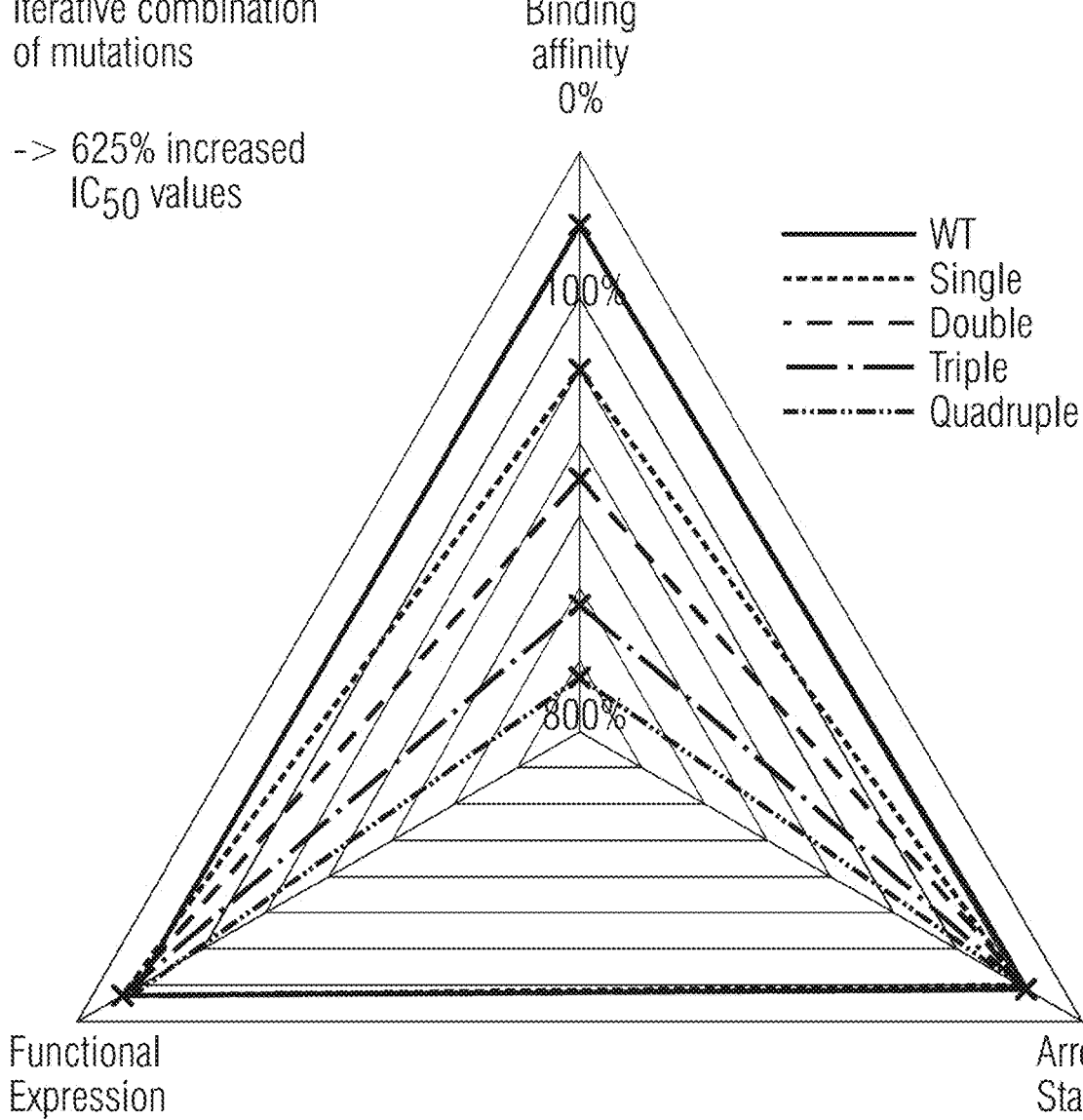
FIG. 5 schematically a systematic construction of an arrestin "Super Binder"

Therefore, the triangular image in FIG. 5 represents the systematic construction of a mutated arrestin having excellent binding properties to the GPCR rhodopsin. These "super binders" are identified by an iterative combination of the mutations of arrestin. For example, those mutant arrestins with a single mutated amino acid position showing in this first class of the single mutated amino acid positions relatively high binding ability are a candidate for the following assay using this single mutated arrestin having now a second mutated amino acid position and so on.

The triangle in FIG. 5 therefore shows in the triangular radar among the binding affinity, the mutant arrestin stability and the functional expression of the mutant arrestin significantly higher values for the $IC_{50}$ especially for those mutant ligands which have three or four mutated amino acid positions as explained above in more detail with reference to FIG. 4.

Spoken more generally, the method according to the present invention therefore can apply an iterative approach, too. In this sense, the starting point is the scan of a ligand having a single mutated amino acid position and observing the respective response in the binding ability. Those of the single mutated ligands having a relatively high binding ability are then the subject for the second assay wherein an additional second amino acid position is mutated. Accordingly, those double mutated ligands showing superior binding ability are the subject for the third assay wherein an additional third amino acid position is mutated, and so on. This iterative approach can therefore be executed until a desired level of biochemical reactivity/binding ability/functional potential is achieved. It has to be noted that the iterative approach can be also executed in the opposite sense searching for multiple mutated ligand that has particularly low biochemical reactivity/binding ability/functional potential as compared to the parent ligand in relationship to the GPCR it binds to.

Figure 6:
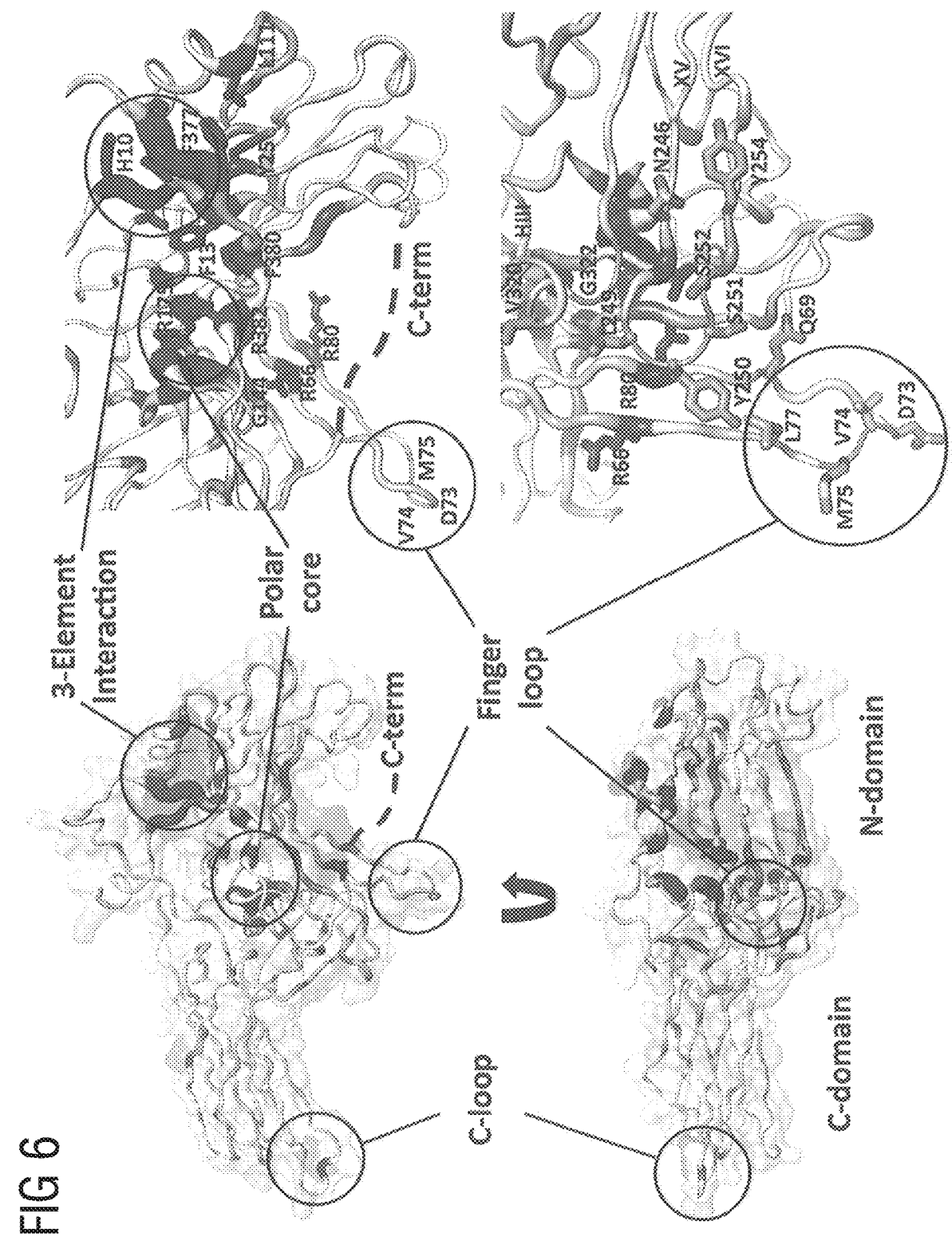
FIG. 6 schematically the arrestin binding mechanism at single amino acid resolution.

The model in FIGS. 6 and 7 show how the arrestin finger loop and beta-strands XV and XVI interact with TM5/TM6 of rhodopsin and act as a sensor for the active receptor conformation. Phosphosensing is achieved by a series of amino acids that anchor the C-tail of arrestin in a position that blocks binding of the receptor (see FIG. 8). In a C-tail exchange mechanism, the C-tail of arrestin is released and subsequently replaced by the phosphorylated C-terminus of the receptor.

FIG. 7 shows the conceptual model of an arrestin-GPCR complex derived from molecular docking of active arrestin and light-activated rhodopsin. The phosphorylated C-terminus of rhodopsin binds along the arrestin N-domain and interacts with several charged residues exposed during release of the arrestin C-terminus. The finger and lariat loops (upper and middle inset) fit into the crevice opening during rhodopsin activation. In this position Gln69 or Asp73 in the arrestin finger loop can interact with Leu72 and Asn73, two residues in TM2 of rhodopsin that are critical for the binding of arrestin-1. The lariat loop mediates contacts to the cytoplasmic ends of TM6 and TM7/H8, two regions whose relative position is involved in biased signaling of β-adrenergic receptors and arrestin binding to rhodopsin. The edge of the C-domain (lower inset) contains a set of amino acids that could interact with the phospholipid membrane or form a secondary binding site for GPCR dimers.

Figure 8:
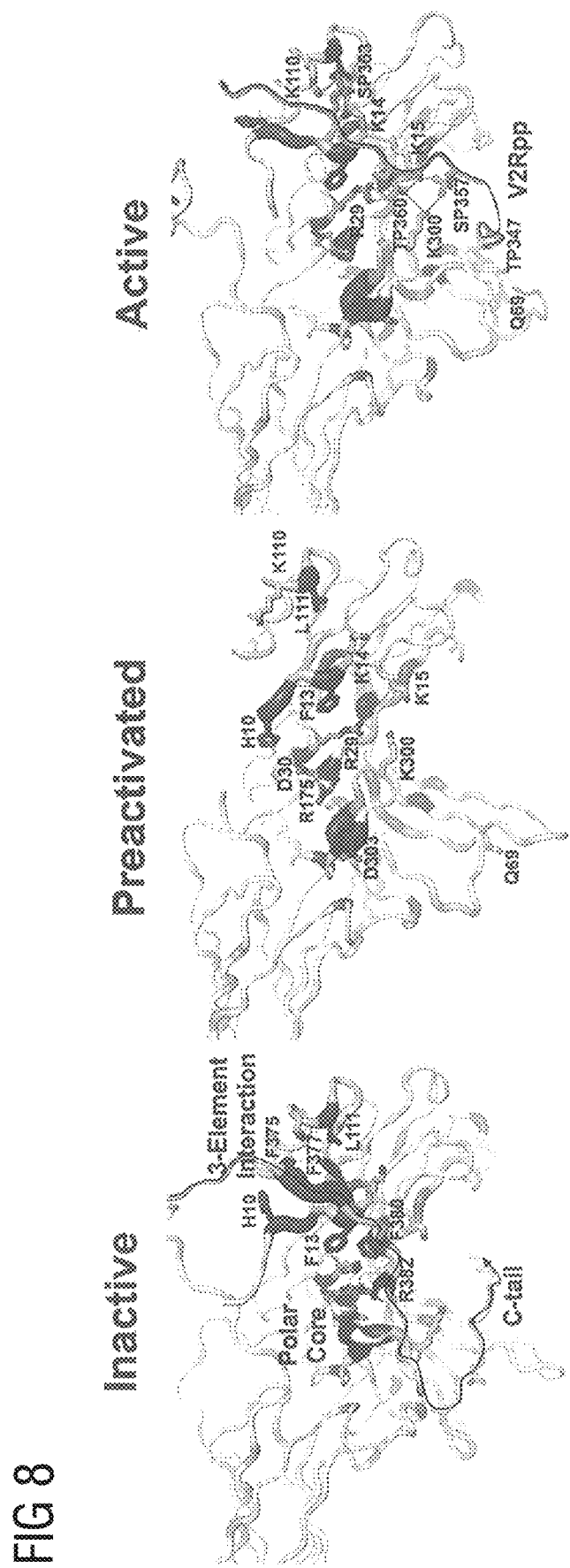
FIG. 8 schematically the C-tail exchange mechanism at single amino acid resolution by which the C-tail of arrestin is replaced by the phosphorylated C-tail of a GPCR.

FIG. 8 shows at single amino acid resolution functional maps of arrestin-1. Binding of 403 arrestin mutants ($IC_{50}$ values shown as increasing ribbon width and as spectrum ranging from red over white to blue) plotted on the crystal structures of inactive[2], preactivated p44 arrestin[3] and an arrestin-1 model based on the crystal structure of arrestin-2 with bound receptor phosphopetide[4]. Several residues including three hydrophobic phenylalanines (F375, F377, F380) and the charged R382 anchor the C-tail of arrestin-1 into the 3-element interaction and polar core regulatory sites. Mutation of these key residues and their interaction partners leads to strongly increased binding to phosphorylated, light activated rhodopsin. Truncation of the C-tail in p44 arrestin leads to a conformational change that releases R29 from the polar core and exposes several other charged residues (K14, K15, Q69, K300) whose mutation leads to strongly reduced binding to phosphorylated rhodopsin. In active arrestin these residues directly interact with phosphorylated serines and threonines in the receptor peptide (green, V2Rpp). Together these data suggest a phosphosensing mechanism in which the C-tail of arrestin-1 is exchanged for the phosphorylated C-terminus of rhodopsin during formation of the desensitizing arrestin complex.

FIG. 9 shows an overview of a transfer of mutations to other arrestins. Specifically, FIG. 9 shows the sequence alignment of bovine arrestin-1 set forth in SEQ ID NO:5 and depicted in FIG. 9 as P08168/ARRS_BOVIN" with human arrestin-1, -2, -3 and -4, set forth in SEQ ID NOS: 1, 2, 3 and 4 and depicted in FIG. 9 as P10523/ARRS_HUMANARRS_HUMAN". P49407/ARRSB1_HUMANARRS_HUMAN", P32121/ARRS_HUMANARRSB2_HUMAN" and P36575/ARRS_HUMANARRC_HUMAN" respectively. The 20 best binders to rhodopsin GPCR are identified in bold letters. Light grey letters which are underscored represent the 20 worst binders to the rhodopsin GPCR.

Table 1 lists the binding parameters for 403 alanine/glycine mutants in arrestin-1.

These finding according to the existing data now can be used to modify the binding of arrestin-2+3 to pharmacological interesting GPCRs. Combination of mutants allows modification of binding affinity and stability of GPCR-arrestin complexes for diagnostic purposes, pharmacological intervention or drug discovery (e.g. beta-arrestin recruitment assays, structure-based drug discovery, silencing of hyperactive GPCRs etc.).

Table 1 below shows a list of $IC_{50}$ values of NaCl on phosphorylated and light-activated rod outer segment (ROS*-P) membrane binding for 403 arrestin mutations covering the complete arrestin-1 sequence. $IC_{50}$ values for each single mutant have been obtained from 8 measurements in increasing concentrations of NaCl (100 mM to 2.4 M) with the quality of fit indicated as $R^2$ and the variation as 95% confidence interval. A selection of functionally important residues has been measured multiple times and the values averaged. 16 mutations listed under remarks have been removed from analysis either because they did not express (as indicated by in gel-fluorescence of the mCherry fluorescence marker) or expression was too low to obtain a reliable signal.

TABLE 1

| Mutant | $IC_{50}$ [M] | Avg. 95% confidence | Quality of fit ($R^2$) | Number of curves | Remarks |
|---|---|---|---|---|---|
| WT | 0.41 | 0.37 to 0.46 | 0.9945 | 59 | |
| K2A | 0.47 | 0.37 to 0.59 | 0.9549 | 1 | |
| A3G | 0.42 | 0.40 to 0.43 | 0.9993 | 1 | |
| N4A | 0.40 | 0.38 to 0.42 | 0.9992 | 1 | |
| K5A | 0.39 | 0.37 to 0.41 | 0.9991 | 1 | |
| P6A | 0.42 | 0.38 to 0.46 | 0.9969 | 1 | |
| A7G | 0.44 | 0.42 to 0.46 | 0.9991 | 1 | |

TABLE 1-continued

| Mutant | IC$_{50}$ [M] | Avg. 95% confidence | Quality of fit (R$^2$) | Number of curves | Remarks |
|---|---|---|---|---|---|
| P8A | 0.40 | 0.38 to 0.42 | 0.9990 | 1 | |
| N9A | 0.34 | 0.31 to 0.38 | 0.9966 | 1 | |
| H10A | 0.65 | 0.60 to 0.71 | 0.9966 | 2 | |
| V11A | 0.61 | 0.56 to 0.67 | 0.9982 | 2 | |
| I12A | 0.47 | 0.43 to 0.52 | 0.9976 | 1 | |
| F13A | 0.84 | 0.74 to 0.95 | 0.9974 | 3 | |
| K14A | 0.30 | 0.26 to 0.33 | 0.9949 | 2 | |
| K15A | 0.33 | 0.30 to 0.38 | 0.9953 | 1 | |
| I16A | 0.33 | 0.31 to 0.35 | 0.9990 | 1 | |
| S17A | 0.40 | 0.38 to 0.42 | 0.9991 | 1 | |
| R18A | 0.33 | 0.28 to 0.38 | 0.9933 | 2 | |
| D19A | 0.44 | 0.42 to 0.45 | 0.9996 | 1 | |
| K20A | 0.34 | 0.32 to 0.37 | 0.9980 | 1 | |
| S21A | 0.40 | 0.38 to 0.42 | 0.9993 | 1 | |
| V22A | 0.41 | 0.40 to 0.42 | 0.9996 | 1 | |
| T23A | 0.43 | 0.37 to 0.50 | 0.9930 | 3 | |
| I24A | 0.24 | 0.18 to 0.34 | 0.9807 | 2 | signal weak |
| Y25A | 0.59 | 0.51 to 0.71 | 0.9949 | 3 | |
| L26A | 0.43 | 0.40 to 0.45 | 0.9990 | 1 | |
| G27A | 0.33 | 0.31 to 0.35 | 0.9981 | 1 | |
| K28A | 0.38 | 0.36 to 0.40 | 0.9987 | 1 | |
| R29A | 0.23 | 0.21 to 0.24 | 0.9965 | 2 | |
| D30A | 0.62 | 0.57 to 0.68 | 0.9974 | 2 | |
| Y31A | 0.43 | 0.32 to 0.40 | 0.9988 | 1 | |
| I32A | 0.33 | 0.30 to 0.37 | 0.9969 | 1 | |
| D33A | 0.39 | 0.38 to 0.40 | 0.9995 | 1 | |
| H34A | 0.32 | 0.29 to 0.35 | 0.9969 | 2 | |
| V35A | 0.32 | 0.29 to 0.35 | 0.9974 | 1 | |
| E36A | 0.40 | 0.38 to 0.42 | 0.9989 | 1 | |
| R37A | 0.32 | 0.30 to 0.35 | 0.9970 | 1 | |
| V38A | 0.37 | 0.35 to 0.39 | 0.9987 | 1 | |
| E39A | 0.37 | 0.35 to 0.39 | 0.9988 | 2 | |
| P40A | 0.37 | 0.36 to 0.40 | 0.9984 | 2 | |
| V41A | 0.40 | 0.37 to 0.43 | 0.9981 | 1 | |
| D42A | 0.40 | 0.36 to 0.45 | 0.9964 | 2 | |
| G43A | 0.50 | 0.45 to 0.55 | 0.9948 | 3 | signal weak |
| V44A | 0.51 | 0.49 to 0.53 | 0.9994 | 2 | |
| V45A | 0.33 | 0.30 to 0.36 | 0.9971 | 1 | |
| L46A | 0.38 | 0.34 to 0.42 | 0.9967 | 1 | |
| V47A | 0.44 | 0.42 to 0.46 | 0.9993 | 1 | |
| D48A | 0.38 | 0.30 to 0.51 | 0.9730 | 2 | |
| P49A | 0.47 | 0.41 to 0.54 | 0.9885 | 1 | |
| E50A | 0.32 | 0.28 to 0.36 | 0.9941 | 1 | |
| L51A | 0.30 | 0.27 to 0.34 | 0.9948 | 1 | |
| V52A | 0.31 | 0.28 to 0.35 | 0.9963 | 1 | |
| K53A | 0.31 | 0.28 to 0.35 | 0.9953 | 1 | |
| G54A | 0.42 | 0.38 to 0.46 | 0.9975 | 1 | |
| K55A | 0.43 | 0.41 to 0.46 | 0.9989 | 1 | |
| R56A | 0.42 | 0.40 to 0.45 | 0.9986 | 1 | |
| V57A | 0.53 | 0.46 to 0.62 | 0.9870 | 2 | signal weak |
| Y58A | 0.35 | 0.33 to 0.38 | 0.9980 | 1 | |
| V59A | 0.42 | 0.46 to 0.50 | 0.9978 | 2 | |
| S60A | 0.48 | 0.46 to 0.50 | 0.9993 | 1 | |
| L61A | 0.35 | 0.29 to 0.43 | 0.9822 | 1 | |
| T62A | 0.31 | 0.27 to 0.36 | 0.9928 | 1 | |
| C63A | 0.41 | 0.36 to 0.76 | 0.9959 | 3 | |
| A64G | 0.45 | 0.43 to 0.47 | 0.9990 | 1 | |
| F65A | 0.47 | 0.45 to 0.50 | 0.9984 | 2 | |
| R66A | 0.64 | 0.59 to 0.69 | 0.9978 | 3 | |
| Y67A | 0.41 | 0.39 to 0.42 | 0.9997 | 1 | |
| G68A | 0.45 | 0.43 to 0.47 | 0.9990 | 1 | |
| Q69A | 0.24 | 0.20 to 0.28 | 0.9873 | 2 | |
| E70A | 0.45 | 0.39 to 0.52 | 0.9852 | 1 | |
| D71A | 0.45 | 0.43 to 0.48 | 0.9979 | 1 | |
| I72A | 0.45 | 0.42 to 0.49 | 0.9963 | 1 | |
| D73A | 0.31 | 0.29 to 0.32 | 0.9992 | 1 | |
| V74A | 0.32 | 0.27 to 0.38 | 0.9875 | 2 | |
| M75A | 0.26 | 0.24 to 0.28 | 0.9980 | 2 | |
| G76A | 0.41 | 0.35 to 0.47 | 0.9947 | 1 | |
| L77A | 0.33 | 0.31 to 0.35 | 0.9980 | 2 | |
| S78A | 0.46 | 0.32 to 0.66 | 0.9495 | 1 | |
| F79A | 0.43 | 0.36 to 0.51 | 0.9903 | 1 | |
| R80A | 0.58 | 0.54 to 0.63 | 0.9984 | 2 | |
| R81A | 0.47 | 0.45 to 0.49 | 0.9989 | 1 | |
| D82A | 0.46 | 0.41 to 0.51 | 0.9959 | 1 | |
| L83A | 0.44 | 0.43 to 0.45 | 0.9997 | 1 | |
| Y84A | 0.51 | 0.48 to 0.54 | 0.9986 | 2 | |
| F85A | 0.48 | 0.43 to 0.53 | 0.9961 | 2 | |
| S86A | 0.47 | 0.44 to 0.51 | 0.9995 | 1 | |
| Q87A | 0.54 | 0.50 to 0.59 | 0.9974 | 2 | |
| V88A | 0.48 | 0.45 to 0.52 | 0.9975 | 1 | |
| Q89A | 0.37 | 0.36 to 0.38 | 0.9998 | 1 | |
| V90A | 0.44 | 0.41 to 0.47 | 0.9979 | 2 | |
| F91A | 0.41 | 0.40 to 0.43 | 0.9994 | 1 | |
| P92A | 0.32 | 0.28 to 0.36 | 0.9931 | 2 | |
| P93A | 0.44 | 0.40 to 0.48 | 0.9978 | 1 | |
| V94A | 0.40 | 0.35 to 0.46 | 0.9927 | 2 | |
| G95A | 0.37 | 0.35 to 0.39 | 0.9990 | 1 | |
| A96G | 0.37 | 0.35 to 0.40 | 0.9984 | 1 | |
| S97A | 0.34 | 0.30 to 0.39 | 0.9947 | 1 | |
| G98A | 0.39 | 0.34 to 0.45 | 0.9944 | 1 | |
| A99G | 0.38 | 0.37 to 0.40 | 0.9993 | 1 | |
| T100A | 0.35 | 0.32 to 0.39 | 0.9962 | 1 | |
| T101A | 0.42 | 0.36 to 0.49 | 0.9918 | 2 | signal weak |
| R102A | 0.35 | 0.30 to 0.39 | 0.9949 | 1 | |
| L103A | 0.48 | 0.42 to 0.55 | 0.9953 | 1 | |
| Q104A | 0.30 | 0.29 to 0.32 | 0.9981 | 1 | |
| E105A | 0.35 | 0.32 to 0.39 | 0.9969 | 1 | |
| S106A | 0.32 | 0.29 to 0.35 | 0.9964 | 1 | |
| L107A | 0.44 | 0.43 to 0.45 | 0.9996 | 1 | |
| I108A | 0.44 | 0.41 to 0.47 | 0.9986 | 1 | |
| K109A | 0.42 | 0.38 to 0.46 | 0.9968 | 1 | |
| K110A | 0.37 | 0.34 to 0.41 | 0.9975 | 1 | |
| L111A | 0.70 | 0.64 to 0.76 | 0.9980 | 2 | |
| G112A | 0.45 | 0.42 to 0.48 | 0.9977 | 1 | |
| A113G | 0.45 | 0.41 to 0.48 | 0.9977 | 1 | |
| N114A | 0.48 | 0.45 to 0.50 | 0.9988 | 1 | |
| T115A | 0.45 | 0.41 to 0.49 | 0.9973 | 1 | |
| Y116A | 0.51 | 0.48 to 0.54 | 0.9975 | 2 | |
| P117A | 0.44 | 0.42 to 0.46 | 0.9992 | 1 | |
| F118A | 0.33 | 0.32 to 0.35 | 0.9990 | 1 | |
| L119A | 0.39 | 0.37 to 0.41 | 0.9989 | 1 | |
| L120A | 0.46 | 0.41 to 0.52 | 0.9910 | 1 | |
| T121A | 0.41 | 0.39 to 0.44 | 0.9988 | 1 | |
| F122A | 0.41 | 0.40 to 0.42 | 0.9999 | 1 | |
| P123A | 0.40 | 0.35 to 0.45 | 0.9947 | 1 | |
| D124A | 0.38 | 0.33 to 0.42 | 0.9956 | 1 | |
| Y125A | 0.37 | 0.35 to 0.41 | 0.9979 | 1 | |
| L126A | 0.41 | 0.38 to 0.44 | 0.9981 | 1 | |
| P127A | 0.33 | 0.30 to 0.38 | 0.9953 | 1 | |
| C128A | 0.40 | 0.33 to 0.49 | 0.9905 | 1 | |
| S129A | 0.53 | 0.47 to 0.60 | 0.9970 | 2 | |
| V130A | 0.41 | 0.37 to 0.45 | 0.9974 | 2 | |
| M131A | 0.39 | 0.37 to 0.41 | 0.9989 | 1 | |
| L132A | 0.47 | 0.45 to 0.49 | 0.9991 | 2 | |
| Q133A | 0.35 | 0.32 to 0.39 | 0.9953 | 1 | |
| P134A | 0.45 | 0.42 to 0.48 | 0.9986 | 1 | |
| A135G | 0.49 | 0.45 to 0.53 | 0.9961 | 3 | |
| P136A | 0.46 | 0.45 to 0.48 | 0.9995 | 1 | |
| Q137A | 0.45 | 0.42 to 0.49 | 0.9952 | 2 | |
| D138A | 0.41 | 0.39 to 0.42 | 0.9995 | 1 | |
| V139A | 0.39 | 0.37 to 0.41 | 0.9988 | 1 | |
| G140A | 0.38 | 0.36 to 0.39 | 0.9991 | 1 | |
| K141A | 0.49 | 0.48 to 0.50 | 0.9998 | 1 | |
| S142A | 0.39 | 0.36 to 0.42 | 0.9976 | 2 | |
| C143A | 0.50 | 0.48 to 0.51 | 0.9997 | 2 | |
| G144A | 0.57 | 0.48 to 0.68 | 0.9921 | 2 | |
| V145A | 0.49 | 0.47 to 0.51 | 0.9994 | 1 | |
| D146A | 0.57 | 0.51 to 0.64 | 0.9947 | 2 | |
| F147A | 0.43 | 0.46 to 0.56 | 0.9945 | 3 | |
| E148A | 0.42 | 0.40 to 0.44 | 0.9988 | 2 | |
| I149A | 0.74 | 0.64 to 0.85 | 0.9901 | 3 | signal weak |
| K150A | 0.42 | 0.40 to 0.44 | 0.9993 | 1 | |
| A151G | 0.35 | 0.34 to 0.36 | 0.9994 | 1 | |
| F152A | 0.42 | 0.37 to 0.46 | 0.9952 | 1 | |
| A153G | 0.32 | 0.31 to 0.34 | 0.9993 | 2 | |
| T154A | 0.44 | 0.35 to 0.55 | 0.9809 | 1 | |
| H155A | 0.35 | 0.32 to 0.38 | 0.9970 | 1 | |
| S156A | 0.33 | 0.31 to 0.36 | 0.9977 | 1 | |
| T157A | 0.62 | 0.55 to 0.70 | 0.9965 | 2 | signal weak |
| D158A | 0.39 | 0.32 to 0.38 | 0.9991 | 1 | |
| V159A | 0.37 | 0.35 to 0.38 | 0.9995 | 1 | |
| E160A | 0.44 | 0.42 to 0.46 | 0.9991 | 1 | |
| E161A | 0.37 | 0.35 to 0.40 | 0.9985 | 1 | |

TABLE 1-continued

| Mutant | IC$_{50}$ [M] | Avg. 95% confidence | Quality of fit (R$^2$) | Number of curves | Remarks |
|---|---|---|---|---|---|
| D162A | 0.40 | 0.38 to 0.42 | 0.9992 | 1 | |
| K163A | 0.43 | 0.40 to 0.47 | 0.9968 | 3 | |
| I164A | 0.41 | 0.38 to 0.44 | 0.9979 | 2 | |
| P165A | 0.42 | 0.38 to 0.46 | 0.9970 | 1 | |
| K166A | 0.38 | 0.33 to 0.42 | 0.9960 | 1 | |
| K167A | 0.36 | 0.34 to 0.39 | 0.9979 | 1 | |
| S168A | 0.48 | 0.46 to 0.51 | 0.9986 | 1 | |
| S169A | 0.46 | 0.42 to 0.50 | 0.9973 | 1 | |
| V170A | 0.58 | 0.51 to 0.66 | 0.9975 | 2 | |
| R171A | 0.54 | 0.47 to 0.61 | 0.9962 | 2 | |
| L172A | 0.28 | 0.26 to 0.30 | 0.9976 | 2 | |
| L173A | 0.51 | 0.47 to 0.55 | 0.9983 | 2 | |
| I174A | 0.38 | 0.36 to 0.40 | 0.9990 | 2 | |
| R175A | 0.91 | 0.77 to 1.08 | 0.9948 | 3 | |
| K176A | 0.47 | 0.43 to 0.51 | 0.9971 | 1 | |
| V177A | 0.33 | 0.29 to 0.37 | 0.9962 | 2 | |
| Q178A | 0.40 | 0.34 to 0.45 | 0.9941 | 1 | |
| H179A | 0.32 | 0.29 to 0.35 | 0.9963 | 2 | |
| A180G | 0.37 | 0.31 to 0.43 | 0.9913 | 1 | |
| P181A | 0.38 | 0.35 to 0.40 | 0.9984 | 1 | |
| R182A | 0.41 | 0.34 to 0.49 | 0.9916 | 1 | |
| D183A | 0.40 | 0.37 to 0.43 | 0.9985 | 1 | |
| M184A | 0.46 | 0.43 to 0.49 | 0.9987 | 1 | |
| G185A | 0.33 | 0.29 to 0.37 | 0.9951 | 1 | |
| P186A | 0.37 | 0.35 to 0.40 | 0.9984 | 1 | |
| Q187A | 0.40 | 0.35 to 0.45 | 0.9957 | 1 | |
| P188A | 0.27 | 0.21 to 0.56 | 0.9973 | 3 | |
| R189A | 0.40 | 0.38 to 0.43 | 0.9988 | 1 | |
| A190G | 0.41 | 0.37 to 0.45 | 0.9974 | 1 | |
| E191A | 0.32 | 0.29 to 0.36 | 0.9961 | 1 | |
| A192G | 0.36 | 0.33 to 0.38 | 0.9982 | 1 | |
| S193A | 0.43 | 0.38 to 0.48 | 0.9962 | 1 | |
| W194A | 0.24 | 0.22 to 0.28 | 0.9899 | 2 | |
| Q195A | 0.33 | 0.31 to 0.36 | 0.9976 | 1 | |
| F196A | 0.30 | 0.27 to 0.34 | 0.9949 | 1 | |
| F197A | 0.31 | 0.28 to 0.34 | 0.9963 | 2 | |
| M198A | 0.32 | 0.28 to 0.36 | 0.9952 | 1 | |
| S199A | 0.31 | 0.28 to 0.33 | 0.9975 | 1 | |
| D200A | 0.42 | 0.38 to 0.46 | 0.9964 | 2 | |
| K201A | 0.40 | 0.37 to 0.43 | 0.9983 | 1 | |
| P202A | 0.35 | 0.31 to 0.39 | 0.9948 | 2 | |
| L203A | 0.39 | 0.35 to 0.43 | 0.9957 | 1 | |
| R204A | 0.44 | 0.41 to 0.46 | 0.9989 | 1 | |
| L205A | 0.40 | 0.38 to 0.42 | 0.9991 | 1 | |
| A206G | 0.36 | 0.34 to 0.39 | 0.9986 | 1 | |
| V207A | 0.42 | 0.40 to 0.44 | 0.9990 | 1 | |
| S208A | 0.41 | 0.39 to 0.42 | 0.9994 | 1 | |
| L209A | 0.47 | 0.42 to 0.51 | 0.9966 | 2 | |
| S210A | 0.35 | 0.33 to 0.37 | 0.9988 | 1 | |
| K211A | 0.40 | 0.38 to 0.43 | 0.9986 | 1 | |
| E212A | 0.46 | 0.42 to 0.50 | 0.9963 | 1 | |
| I213A | 0.36 | 0.34 to 0.38 | 0.9985 | 1 | |
| Y214A | 0.37 | 0.35 to 0.39 | 0.9988 | 1 | |
| Y215A | 0.42 | 0.34 to 0.50 | 0.9918 | 1 | |
| H216A | 0.40 | 0.38 to 0.42 | 0.9988 | 1 | |
| G217A | 0.36 | 0.34 to 0.38 | 0.9986 | 1 | |
| E218A | 0.42 | 0.41 to 0.44 | 0.9995 | 1 | |
| P219A | 0.44 | 0.41 to 0.46 | 0.9985 | 1 | |
| I220A | 0.53 | 0.46 to 0.61 | 0.9895 | 2 | signal weak |
| P221A | 0.43 | 0.40 to 0.46 | 0.9981 | 1 | |
| V222A | 0.51 | 0.48 to 0.53 | 0.9989 | 3 | |
| T223A | 0.41 | 0.38 to 0.43 | 0.9985 | 1 | |
| V224A | 0.51 | 0.39 to 0.67 | 0.9416 | 2 | signal weak |
| A225G | 0.44 | 0.41 to 0.47 | 0.9983 | 1 | |
| V226A | 0.54 | 0.45 to 0.66 | 0.9856 | 5 | signal weak |
| T227A | 0.38 | 0.37 to 0.40 | 0.9991 | 1 | |
| N228A | 0.34 | 0.32 to 0.37 | 0.9975 | 1 | |
| S229A | 0.31 | 0.29 to 0.34 | 0.9971 | 1 | |
| T230A | 0.42 | 0.41 to 0.43 | 0.9996 | 1 | |
| E231A | 0.48 | 0.46 to 0.50 | 0.9994 | 1 | |
| K232A | 0.31 | 0.27 to 0.53 | 0.9970 | 3 | |
| T233A | 0.36 | 0.33 to 0.38 | 0.9978 | 1 | |
| V234A | 0.31 | 0.29 to 0.33 | 0.9987 | 1 | |
| K235A | 0.34 | 0.32 to 0.37 | 0.9976 | 1 | |
| K236A | 0.40 | 0.37 to 0.44 | 0.9979 | 1 | |
| I237A | 0.40 | 0.37 to 0.43 | 0.9974 | 1 | |
| K238A | 0.40 | 0.35 to 0.46 | 0.9946 | 1 | |
| V239A | 0.38 | 0.36 to 0.40 | 0.9988 | 1 | |
| L240A | 0.44 | 0.40 to 0.48 | 0.9961 | 1 | |
| V241A | — | — | — | 5 | no expression |
| E242A | 0.36 | 0.34 to 0.37 | 0.9992 | 1 | |
| Q243A | 0.40 | 0.38 to 0.41 | 0.9992 | 1 | |
| V244A | 0.39 | 0.37 to 0.41 | 0.9990 | 1 | |
| T245A | 0.38 | 0.35 to 0.40 | 0.9978 | 1 | |
| N246A | 0.36 | 0.33 to 0.40 | 0.9960 | 2 | |
| V247A | 0.59 | 0.55 to 0.62 | 0.9989 | 2 | |
| V248A | 0.40 | 0.38 to 0.42 | 0.9991 | 1 | |
| L249A | 0.31 | 0.28 to 0.33 | 0.9968 | 3 | |
| Y250A | 0.31 | 0.27 to 0.48 | 0.9938 | 3 | |
| S251A | 0.33 | 0.31 to 0.35 | 0.9975 | 3 | |
| S252A | 0.32 | 0.31 to 0.33 | 0.9995 | 1 | |
| D253A | 0.50 | 0.45 to 0.56 | 0.9912 | 1 | |
| Y254A | 0.31 | 0.26 to 0.36 | 0.9913 | 1 | |
| Y255A | 0.44 | 0.42 to 0.46 | 0.9988 | 1 | |
| I256A | 0.44 | 0.39 to 0.48 | 0.9957 | 2 | |
| K257A | 0.50 | 0.46 to 0.55 | 0.9968 | 2 | |
| T258A | — | — | — | 5 | no expression |
| V259A | 0.40 | 0.37 to 0.42 | 0.9983 | 1 | |
| A260G | 0.41 | 0.37 to 0.44 | 0.9975 | 1 | |
| A261G | 0.46 | 0.43 to 0.49 | 0.9986 | 2 | |
| E262A | 0.33 | 0.31 to 0.35 | 0.9986 | 1 | |
| E263A | 0.47 | 0.43 to 0.51 | 0.9963 | 1 | |
| A264G | 0.37 | 0.36 to 0.39 | 0.9992 | 1 | |
| Q265A | 0.42 | 0.33 to 0.53 | 0.9822 | 1 | |
| E266A | 0.35 | 0.30 to 0.41 | 0.9919 | 1 | |
| K267A | 0.36 | 0.29 to 0.45 | 0.9863 | 1 | |
| V268A | 0.40 | 0.38 to 0.43 | 0.9984 | 1 | |
| P269A | 0.42 | 0.39 to 0.46 | 0.9972 | 1 | |
| P270A | 0.32 | 0.21 to 0.48 | 0.9631 | 1 | |
| N271A | 0.39 | 0.37 to 0.42 | 0.9979 | 1 | |
| S272A | 0.36 | 0.32 to 0.40 | 0.9964 | 1 | |
| S273A | 0.38 | 0.35 to 0.43 | 0.9966 | 1 | |
| L274A | 0.40 | 0.37 to 0.43 | 0.9984 | 1 | |
| T275A | 0.42 | 0.39 to 0.45 | 0.9982 | 1 | |
| K276A | 0.39 | 0.36 to 0.42 | 0.9972 | 1 | |
| T277A | 0.53 | 0.48 to 0.69 | 0.9990 | 1 | |
| L278A | 0.46 | 0.43 to 0.49 | 0.9985 | 1 | |
| T279A | 0.39 | 0.36 to 0.43 | 0.9974 | 1 | |
| L280A | 0.32 | 0.27 to 0.37 | 0.9866 | 1 | |
| V281A | 0.41 | 0.38 to 0.45 | 0.9975 | 1 | |
| P282A | 0.30 | 0.28 to 0.32 | 0.9975 | 3 | |
| L283A | 0.35 | 0.33 to 0.38 | 0.9977 | 1 | |
| L284A | 0.56 | 0.51 to 0.60 | 0.9986 | 2 | |
| A285G | 0.35 | 0.32 to 0.38 | 0.9971 | 1 | |
| N286A | 0.40 | 0.37 to 0.42 | 0.9985 | 1 | |
| N287A | 0.33 | 0.31 to 0.35 | 0.9982 | 1 | |
| R288A | 0.39 | 0.37 to 0.42 | 0.9989 | 1 | |
| E289A | 0.41 | 0.37 to 0.45 | 0.9973 | 1 | |
| R290A | 0.45 | 0.41 to 0.49 | 0.9979 | 1 | |
| R291A | 0.56 | 0.51 to 0.62 | 0.9967 | 2 | |
| G292A | 0.40 | 0.35 to 0.47 | 0.9939 | 1 | |
| I293A | 0.34 | 0.26 to 0.45 | 0.9786 | 1 | |
| A294G | 0.37 | 0.33 to 0.43 | 0.9951 | 1 | |
| L295A | 0.44 | 0.41 to 0.48 | 0.9979 | 2 | |
| D296A | 0.92 | 0.71 to 1.21 | 0.9860 | 3 | |
| G297A | 1.14 | 0.82 to 1.75 | 0.9879 | 3 | |
| K298A | 0.52 | 0.41 to 0.66 | 0.9906 | 2 | |
| I299A | 0.32 | 0.29 to 0.36 | 0.9956 | 1 | |
| K300A | 0.33 | 0.31 to 0.35 | 0.9983 | 1 | |
| H301A | 0.35 | 0.32 to 0.39 | 0.9968 | 1 | |
| E302A | 0.41 | 0.36 to 0.47 | 0.9940 | 2 | |
| D303A | 0.87 | 0.76 to 0.99 | 0.9964 | 3 | |
| T304A | 0.84 | 0.74 to 0.96 | 0.9967 | 3 | |
| N305A | 0.34 | 0.33 to 0.35 | 0.9997 | 1 | |
| L306A | 0.36 | 0.35 to 0.37 | 0.9998 | 1 | |
| A307G | 0.64 | 0.57 to 0.72 | 0.9967 | 2 | |
| S308A | 0.31 | 0.31 to 0.32 | 0.9999 | 1 | |
| S309A | 0.39 | 0.37 to 0.41 | 0.9986 | 1 | |
| T310A | 0.46 | 0.41 to 0.53 | 0.9893 | 1 | |
| I311A | 0.37 | 0.35 to 0.38 | 0.9991 | 1 | |
| I312A | 0.41 | 0.19 to 0.88 | 0.9593 | 1 | |
| K313A | 0.42 | 0.41 to 0.43 | 0.9996 | 1 | |
| E314A | 0.35 | 0.34 to 0.37 | 0.9993 | 1 | |
| G315A | 0.42 | 0.40 to 0.43 | 0.9995 | 1 | |

TABLE 1-continued

| Mutant | IC$_{50}$ [M] | Avg. 95% confidence | Quality of fit (R$^2$) | Number of curves | Remarks |
|---|---|---|---|---|---|
| I316A | 0.40 | 0.39 to 0.41 | 0.9996 | 1 | |
| D317A | 0.49 | 0.46 to 0.52 | 0.9984 | 1 | |
| K318A | 0.36 | 0.35 to 0.37 | 0.9996 | 1 | |
| T319A | 0.43 | 0.39 to 0.47 | 0.9976 | 1 | |
| V320A | 0.25 | 0.24 to 0.27 | 0.9979 | 2 | |
| M321A | 0.40 | 0.34 to 0.47 | 0.9930 | 1 | |
| G322A | 0.20 | 0.04 to 0.73 | 0.8993 | 3 | signal weak |
| I323A | 0.32 | 0.31 to 0.33 | 0.9993 | 1 | |
| L324A | 0.44 | 0.42 to 0.45 | 0.9994 | 1 | |
| V325A | — | — | — | 7 | no expression |
| S326A | 0.38 | 0.35 to 0.41 | 0.9980 | 2 | |
| Y327A | — | — | — | 7 | no expression |
| Q328A | 0.45 | 0.41 to 0.50 | 0.9969 | 1 | |
| I329A | 0.45 | 0.44 to 0.46 | 0.9998 | 1 | |
| K330A | 0.41 | 0.38 to 0.43 | 0.9985 | 1 | |
| V331A | 0.41 | 0.40 to 0.43 | 0.9994 | 1 | |
| K332A | 0.46 | 0.44 to 0.48 | 0.9992 | 1 | |
| L333A | 0.39 | 0.36 to 0.43 | 0.9969 | 1 | |
| T334A | 0.40 | 0.39 to 0.41 | 0.9997 | 1 | |
| V335A | 0.40 | 0.38 to 0.42 | 0.9991 | 1 | |
| S336A | 0.36 | 0.35 to 0.37 | 0.9993 | 1 | |
| G337A | 0.29 | 0.28 to 0.31 | 0.9988 | 2 | |
| L338A | 0.38 | 0.34 to 0.42 | 0.9955 | 2 | |
| L339A | 0.30 | 0.27 to 0.34 | 0.9954 | 2 | |
| G340A | 0.39 | 0.36 to 0.42 | 0.9976 | 1 | |
| E341A | 0.57 | 0.52 to 0.63 | 0.9961 | 2 | |
| L342A | 0.40 | 0.30 to 0.34 | 0.9969 | 2 | |
| T343A | 0.32 | 0.31 to 0.33 | 0.9992 | 1 | |
| S344A | 0.40 | 0.39 to 0.42 | 0.9996 | 1 | |
| S345A | 0.34 | 0.33 to 0.36 | 0.9988 | 1 | |
| E346A | 0.46 | 0.42 to 0.50 | 0.9946 | 1 | |
| V347A | 0.36 | 0.35 to 0.38 | 0.9994 | 1 | |
| A348G | 0.41 | 0.39 to 0.43 | 0.9990 | 1 | |
| T349A | 0.30 | 0.29 to 0.32 | 0.9990 | 1 | |
| E350A | 0.40 | 0.39 to 0.42 | 0.9996 | 1 | |
| V351A | 0.43 | 0.40 to 0.45 | 0.9985 | 1 | |
| P352A | 0.39 | 0.37 to 0.40 | 0.9993 | 1 | |
| F353A | 0.52 | 0.47 to 0.58 | 0.9942 | 1 | |
| R354A | 0.34 | 0.28 to 0.42 | 0.9859 | 2 | |
| L355A | 0.45 | 0.42 to 0.48 | 0.9978 | 1 | |
| M356A | 0.37 | 0.36 to 0.38 | 0.9997 | 1 | |
| H357A | 0.48 | 0.45 to 0.51 | 0.9975 | 1 | |
| P358A | 0.35 | 0.34 to 0.36 | 0.9997 | 1 | |
| Q359A | 0.44 | 0.43 to 0.45 | 0.9997 | 1 | |
| P360A | 0.38 | 0.35 to 0.42 | 0.9968 | 1 | |
| E361A | 0.44 | 0.43 to 0.44 | 0.9999 | 1 | |
| D362A | 0.45 | 0.41 to 0.50 | 0.9946 | 1 | |
| P363A | 0.44 | 0.43 to 0.46 | 0.9994 | 1 | |
| D364A | 0.44 | 0.43 to 0.45 | 0.9996 | 1 | |
| T365A | 0.41 | 0.38 to 0.44 | 0.9979 | 1 | |
| A366G | 0.43 | 0.41 to 0.46 | 0.9985 | 1 | |
| K367A | 0.41 | 0.39 to 0.43 | 0.9993 | 1 | |
| E368A | 0.44 | 0.41 to 0.47 | 0.9976 | 1 | |
| S369A | 0.43 | 0.41 to 0.47 | 0.9992 | 1 | |
| F370A | 0.46 | 0.44 to 0.49 | 0.9984 | 1 | |
| Q371A | 0.36 | 0.35 to 0.37 | 0.9994 | 1 | |
| D372A | 0.42 | 0.41 to 0.42 | 0.9998 | 1 | |
| E373A | 0.44 | 0.43 to 0.45 | 0.9998 | 1 | |
| N374A | 0.34 | 0.30 to 0.39 | 0.9932 | 2 | |
| F375A | 1.28 | 0.93 to 1.88 | 0.9916 | 4 | |
| V376A | 0.66 | 0.58 to 0.75 | 0.9957 | 3 | |
| F377A | 1.08 | 0.82 to 1.43 | 0.9949 | 3 | |
| E378A | 0.47 | 0.45 to 0.49 | 0.9992 | 1 | |
| E379A | 0.43 | 0.42 to 0.44 | 0.9998 | 1 | |
| F380A | 1.00 | 0.70 to 1.45 | 0.9903 | 3 | |
| A381G | 0.46 | 0.37 to 0.59 | 0.9592 | 2 | signal weak |
| R382A | 0.97 | 0.76 to 1.24 | 0.9944 | 4 | |
| Q383A | 0.39 | 0.37 to 0.42 | 0.9987 | 2 | |
| N384A | 0.35 | 0.33 to 0.37 | 0.9988 | 1 | |
| L385A | 0.44 | 0.41 to 0.48 | 0.9966 | 1 | |
| K386A | 0.40 | 0.39 to 0.41 | 0.9996 | 1 | |
| D387A | 0.46 | 0.43 to 0.49 | 0.9978 | 1 | |
| A388G | 0.40 | 0.37 to 0.45 | 0.9971 | 1 | |
| G389A | 0.40 | 0.38 to 0.42 | 0.9987 | 1 | |
| E390A | 0.41 | 0.36 to 0.48 | 0.9929 | 2 | |
| Y391A | 0.41 | 0.39 to 0.44 | 0.9983 | 1 | |
| K392A | 0.37 | 0.35 to 0.39 | 0.9989 | 1 | |
| E393A | 0.42 | 0.40 to 0.44 | 0.9991 | 1 | |
| E394A | 0.44 | 0.41 to 0.49 | 0.9973 | 2 | |
| K395A | 0.44 | 0.29 to 0.70 | 0.9495 | 3 | signal weak |
| T396A | 0.45 | 0.43 to 0.46 | 0.9996 | 1 | |
| D397A | 0.41 | 0.38 to 0.45 | 0.9981 | 2 | |
| Q398A | 0.34 | 0.30 to 0.38 | 0.9958 | 1 | |
| E399A | 0.35 | 0.32 to 0.40 | 0.9959 | 1 | |
| A400G | 0.36 | 0.32 to 0.41 | 0.9957 | 1 | |
| A401G | 0.34 | 0.30 to 0.39 | 0.9947 | 1 | |
| M402A | 0.40 | 0.36 to 0.44 | 0.9962 | 2 | |
| D403A | 0.43 | 0.40 to 0.46 | 0.9984 | 1 | |
| E404A | 0.41 | 0.36 to 0.46 | 0.9962 | 1 | |

The following mutants were constructed earlier and belong to prior art: K2A[3], I12A[4], K14A[4], K15A[4], R18A[5], Y25A[6], D30A[3], V44A[6], L46A[6], F65A[5], D72A[7], R102A[6], L103A[6], Q104A[6], E105A[6], S106A[6], L107A[6], I108A[6], K109A[6], K110A[6], L111A[6], D138A[5], K142A[7], D162A[5], K166A[5], V170A[1], L172A[1], L173A[1], I174A[1], R175A[1], V177A[1], Q178A[1], K235A[5], Y250A[5], E346A[5], D296A[3], D303A[3], F375A[2], V376A[2], F377A[2], F380A[2], R382A[3]

The earlier described mutants were analyzed in one-point measurements for binding to different states of rhodopsin. IC50 values of sodium chloride were not derived earlier for those mutants.

[1] Gurevich & Benovic, 1996: Mechanism of phosphorylation-recognition by visual arrestin and the transition of arrestin into a high affinity binding state.

[2] Gurevich, 1998: The selectivity of visual arrestin for light-activated phosphorhodopsin is controlled by multiple nonredundant mechanisms.

[3] Vishnivetskiy, Paz, Schubert, Hirsch & Gurevich, 1999: How does arrestin respond to the phosphorylated state of rhodopsin?

[4] Vishnivetskiy, Schubert, Climaco, Gurevich, Velez, Gurevich, 2000: An additional phosphate-binding element in arrestin molecule: Implications for the mechanism of arrestin activation.

[5] Hanson & Gurevich, 2005: The differential engagement of arrestin surface charges by the various functional forms of the receptor.

[6] Vishnivetskiy, Francis, Eps, Kim, Hanson, Klug, Hubbell, Gurevich, 2010: The role of arrestin alpha-helix I in receptor binding.

[7] Vishnivetskiy, Baameur, Findley and Gurevich, 2013: Critical role of the central 139-loop in stability and binding selectivity of arrestin-1

DETAILED INFORMATION ON THE EXPERIMENTAL WORK

Mutants were expressed and cells disrupted in buffer C [10 mM Hepes (pH 7.0), 100 mM NaCl, 1 mM DTT, 1 mM MgCl$_2$, and 0.1 mM EDTA] or buffer D (containing 1.842 M NaCl), both supplemented with 0.2 mg/mL lysozyme, 20 µg/mL DNase, 1.5 mM PMSF, and protease inhibitor mixture Roche Complete. Procedure C using buffer C and plate C was applied to wild type, single and combined mutants of the arrestin-mCherry construct. Procedure D using buffer D and plate D was applied to single mutant F375A and to combined mutants of the arrestin-mCherry construct. In detail, 1.024 mL cleared cell lysate containing wild type or mutant arrestin-mCherry construct in buffer C was mixed with 76 µL ROS-P*, while 637.1 µL cleared cell lysate in buffer D was mixed with 82.9 μL of the same ROS-P* (1.45 mg/mL) stock, obtaining master mixes C or D, respectively. Master mix C was distributed in 100-μL portions to 8 wells of a 96-well plate (in the following called plate C) with each well containing 100 μL buffer C with increasing amounts of sodium chloride, finally yielding 100, 247, 492, 737, and 982 mM and 1.472, 1.962, and 2.403 M NaCl in the 8 reaction mixes. Each plate C contained wild type arrestin-mCherry for reference and 11 different arrestin-mCherry mutants. Master mix D was portioned in 60-μL fractions and transferred to 8 wells of a 96-well plate (below called plate D) with each well containing 140 μL of the same buffer with different amounts of sodium chloride, resulting in 492, 737, and 982 mM and 1.472, 1.962, 2.403, 3.176, and 3.949 M NaCl. 11 different arrestin-mCherry mutants were assayed with each plate C, containing arrestin-mCherry wild type construct (as reference), and the same amount of mutants with each plate D, containing arrestin-mCherry mutant F375A (as reference). Samples in each well were mixed, at 37° C. for 5 min incubated and for 6 min light activated. Separate 96-well plates were filled with the following samples and processed in parallel in the dark: one 100-μL fraction of each master mix C was combined with 100 μL buffer C or one 60-μL portion of each master mix D with 140 μL buffer which was supplemented with NaCl to yield 492 mM NaCl. All plates were centrifuged and supernatants removed and pellets washed by carefully adding 100 μL buffer C to plates C or 100 μL buffer with 492 mM NaCl to plates D. Dark controls were treated accordingly. Pellets in plates C were resuspended with buffer C and pellets in plates D with buffer containing 492 mM NaCl. Quantification of pulled-down arrestin-mCherry was conducted. Table 2 lists the constructed mutants and includes the number of measurements and thereof derived $IC_{50}$ and $R^2$ values as well as 95% confidence intervals.

In-Gel Fluorescence Thermo-Stability Assay.

Arrestin-mCherry fusion proteins were expressed, harvested and lysed. The cell lysate from a 50-mL cell-culture fraction was cleared by centrifugation (Centrifuge 5424R; Eppendorf) at 21,100×g for 20 min at 4° C. The lysate was distributed in 100-μL portions to eleven 1.5-mL tubes (Sarstedt), which were put into a heating block (Dri-Block; Techne) that was equilibrated at 30° C. The temperature was ramped up to 80° C. manually in 5° C.-steps each 2.5 min. Samples were removed successively all 2.5 min and cooled down on ice. Precipitant was removed by centrifugation for 1 h. 12 μL supernatant of each sample were mixed with 3 μL 5×SDS-loading dye. Full-length arrestin-mCherry construct was separated from degraded protein by SDS-PAGE for 1 h at 200 V and 80 mA in MOPS buffer using an 8-12% Bis-Tris gradient gel (Novex NuPAGE; Life Technologies) in supplied chamber (Novex NuPAGE SDS-PAGE gel system; Life Technologies). Fluorescence-emission of mCherry or mCherry-protein fusions was detected by exciting the protein at 312 or 365 nm using a 605 nm-filter (ImageQuant RT ECL; GE Healthcare). Fluorescence intensities were quantified by ImageJ (NIH) and plotted in Prism. Boltzmann sigmoidal fitting allowed to determine melting temperatures ($T_M$) and $R^2$ values and standard errors. $T_M$ values of wild type, V170A, L173A and R175A derived by described novel in-gel fluorescence thermostability assay were compared with $T_M$ values derived by a standard thermo-shift assay utilizing the fluorescent dye CPM, N-[4-(7-diethylamino-4-methyl-3-coumarinyl)phenyl]malemeide. The in-gel fluorescence thermostability assay is superior to the CPM assay in terms of simplicity: It does not require protein purification and uses cheaper instrumentation also available in low-budget laboratories.

The following table 2 shows a list of constructed mutants that were screened for half-maximal inhibitory concentration ($IC_{50}$) of NaCl to disrupt formation of complexes with P-R*. Binding of each mutant to P-R* in its natural environment, the rod outer segment (ROS) membranes, was quantified in 8 different sodium chloride concentrations, ranging from 100 to 2403 mM. The measurement was repeated for the range from 492 to 3949 mM salt if the fitted sigmoidal dose-response curve could not reach the bottom plateau. The number of test sets is indicated from which $IC_{50}$, $R^2$ and 95% confidence interval were derived. It is remarked if expression of functional arrestin protein was too low to determine $IC_{50}$ values reliably. The melting temperature of arrestin mutants ($T_M$) was determined by above described in-gel fluorescence assay.

TABLE 2

List of constructed mutants that were screened for half-maximal inhibitory concentration ($IC_{50}$) as also shown in FIG. 4.

Arrestin-1 mutants

| Mutant | $IC_{50}$ [M] | 95% confidence interval | Quality of fit ($R^2$) | Number of curves | Func. expression level [%] | $T_M$ (arrestin) [° C.] (No of measurements) |
|---|---|---|---|---|---|---|
| WT | 0.41 | 0.37 to 0.46 | 0.9937 | 74 | 100 ± 53 | 64 ± 1 (10) |
| V11A | 0.61 | 0.56 to 0.67 | 0.9982 | 2 | 50-150 | 62 ± 1 (2) |
| F13A | 0.84 | 0.74 to 0.95 | 0.9974 | 3 | 50-150 | 57 ± 2 (1) |
| Y25A | 0.59 | 0.51 to 0.71 | 0.9949 | 3 | 50-150 | 61 ± 0 (1) |
| V44A | 0.51 | 0.49 to 0.53 | 0.9994 | 2 | 50-150 | 64 ± 1 (1) |
| R66A | 0.64 | 0.59 to 0.69 | 0.9978 | 3 | 50-150 | 59 ± 1 (1) |
| Q87A | 0.54 | 0.50 to 0.59 | 0.9974 | 2 | 50-150 | weak signal |
| L111A | 0.70 | 0.64 to 0.76 | 0.9980 | 2 | 50-150 | 61 ± 1 (1) |
| C143A | 0.50 | 0.48 to 0.51 | 0.9997 | 2 | 50-150 | weak signal |
| G144A | 0.57 | 0.48 to 0.68 | 0.9921 | 2 | 50-150 | 60 ± 0 (1) |
| I149A | 0.74 | 0.64 to 0.85 | 0.9901 | 3 | ≤20 | weak signal |
| V170A | 0.58 | 0.51 to 0.66 | 0.9975 | 2 | 50-150 | 60 ± 1 (2) |
| R171A | 0.54 | 0.47 to 0.61 | 0.9962 | 2 | 50-150 | 60 ± 1 (1) |
| L173A | 0.51 | 0.47 to 0.55 | 0.9983 | 2 | 50-150 | 62 ± 1 (1) |
| R175A | 0.91 | 0.77 to 1.08 | 0.9948 | 3 | 50-150 | 53 ± 1 (2) |
| V247A | 0.59 | 0.55 to 0.62 | 0.9989 | 2 | 50-150 | 54 ± 1 (1) |
| R291A | 0.56 | 0.51 to 0.62 | 0.9967 | 2 | 50-150 | 63 ± 0 (1) |
| D296A | 0.92 | 0.71 to 1.21 | 0.9860 | 3 | 50-150 | 59 ± 1 (2) |

TABLE 2-continued

List of constructed mutants that were screened
for half-maximal inhibitory concentration
(IC$_{50}$) as also shown in FIG. 4.
Arrestin-1 mutants

| Mutant | IC$_{50}$ [M] | 95% confidence interval | Quality of fit (R$^2$) | Number of curves | Func. expression level [%] | T$_M$ (arrestin) [° C.] (No of measurements) |
|---|---|---|---|---|---|---|
| G297A | 1.14 | 0.82 to 1.75 | 0.9879 | 3 | 50-150 | 53 ± 1 (1) |
| K298A | 0.52 | 0.41 to 0.66 | 0.9906 | 2 | 50-150 | 64 ± 0 (1) |
| D303A | 0.87 | 0.76 to 0.99 | 0.9964 | 3 | 50-150 | 55 ± 1 (1) |
| T304A | 0.84 | 0.74 to 0.96 | 0.9967 | 3 | 50-150 | 60 ± 1 (2) |
| A307G | 0.64 | 0.57 to 0.72 | 0.9967 | 2 | 50-150 | 57 ± 0 (3) |
| E341A | 0.57 | 0.52 to 0.63 | 0.9961 | 2 | 50-150 | 63 ± 1 (2) |
| F375A | 1.32 | 0.94 to 1.95 | 0.9849 | 23 | 107 ± 26 | 63 ± 1 (3) |
| V376A | 0.66 | 0.58 to 0.75 | 0.9957 | 3 | 50-150 | 62 ± 1 (1) |
| F377A | 1.08 | 0.82 to 1.43 | 0.9949 | 3 | ≥150 | 66 ± 1 (2) |
| F380A | 1.00 | 0.70 to 1.45 | 0.9903 | 3 | ≥150 | 55 ± 0 (1) |
| R382A | 0.97 | 0.76 to 1.24 | 0.9944 | 4 | 50-150 | 62 ± 1 (1) |
| H10A + F375A | 1.54 | 1.40 to 1.69 | 0.9967 | 2 | 50-150 | |
| V11A + F375A | 0.99 | 0.64 to 1.67 | 0.9805 | 2 | 50-150 | 60 ± 1 (1) |
| F13A + F375A | 1.02 | 0.91 to 1.16 | 0.9968 | 2 | 50-150 | |
| I24A + F375A | 1.39 | 0.95 to 2.02 | 0.9884 | 2 | ≤30 | |
| Y25A + F375A | 1.10 | 0.92 to 1.31 | 0.9958 | 3 | 50-150 | |
| D30A + F375A | 1.41 | 0.87 to 2.34 | 0.9893 | 3 | 50-150 | |
| V44A + F375A | 1.69 | 1.07 to 2.80 | 0.9871 | 3 | ≤30 | |
| P49A + F375A | 1.75 | 0.81 to 4.18 | 0.9660 | 3 | ≤30 | |
| R56A + F375A | 1.45 | 1.14 to 1.85 | 0.9968 | 3 | 50-150 | |
| V57A + F375A | 2.17 | 1.25 to 3.83 | 0.9743 | 3 | ≤30 | |
| V59A + F375A | 1.92 | 1.29 to 2.96 | 0.9806 | 3 | ≤30 | |
| A64G + F375A | 1.16 | 0.78 to 1.75 | 0.9907 | 3 | 50-150 | |
| R66A + F375A | 2.04 | 1.08 to 3.89 | 0.9674 | 3 | 50-150 | 59 ± 1 (2) |
| R80A + F375A | — | — | — | 3 | <detection | |
| F85A + F375A | 1.02 | 0.65 to 1.71 | 0.9883 | 2 | 50-150 | |
| Q87A + F375A | 2.01 | 1.33 to 3.10 | 0.9890 | 2 | ≤30 | |
| L107A + F375A | 1.27 | 0.81 to 2.00 | 0.9834 | 2 | ≤30 | |
| L111A + F375A | 1.53 | 0.74 to 3.55 | 0.9796 | 2 | 50-150 | |
| D124A + F375A | 1.08 | 0.87 to 1.37 | 0.9942 | 2 | 50-150 | |
| C128A + F375A | 1.19 | 1.00 to 1.42 | 0.9975 | 2 | 50-150 | |
| C143A + F375A | 1.03 | 1.00 to 1.18 | 0.9969 | 3 | 50-150 | |
| G144A + F375A | 1.48 | 0.85 to 2.78 | 0.9888 | 3 | 50-150 | |
| V145A + F375A | — | — | — | 3 | <detection | |
| D146A + F375A | 1.53 | 1.30 to 1.80 | 0.9916 | 2 | 50-150 | |
| F147A + F375A | — | — | — | 3 | <detection | |
| I149A + F375A | 2.24 | 1.62 to 3.09 | 0.9844 | 2 | ≤30 | 50 ± 2 (2) |
| K163A + F375A | 1.19 | 0.65 to 2.16 | 0.9866 | 3 | 50-150 | |
| V170A + F375A | 1.06 | 0.70 to 1.70 | 0.9866 | 4 | 50-150 | weak signal (1) |
| R171A + F375A | 1.73 | 1.29 to 2.34 | 0.9844 | 2 | 50-150 | |
| L173A + F375A | 1.58 | 1.34 to 1.87 | 0.9921 | 2 | 50-150 | |
| R175A + F375A | 2.48 | 1.55 to 4.21 | 0.9723 | 3 | 50-150 | |
| D183A + F375A | 0.98 | 0.67 to 1.43 | 0.9927 | 1 | 50-150 | |
| V222A + F375A | 0.44 | 0.39 to 0.49 | 0.9949 | 1 | ≤30 | |
| A225G + F375A | 1.42 | 0.73 to 3.51 | 0.9738 | 2 | 50-150 | |
| V247A + F375A | — | — | — | 3 | ≤30 | |
| D253A + F375A | 1.22 | 1.00 to 1.50 | 0.9968 | 3 | 50-150 | |
| I256A + F375A | 1.23 | 0.83 to 1.84 | 0.9866 | 2 | 50-150 | |
| K257A + F375A | 1.45 | 1.11 to 1.91 | 0.9947 | 2 | 50-150 | |
| A261G + F375A | 1.46 | 0.84 to 2.74 | 0.9897 | 3 | 50-150 | |
| S272A + F375A | 1.57 | 1.35 to 1.84 | 0.9931 | 2 | 50-150 | |
| R291A + F375A | 1.42 | 0.91 to 2.40 | 0.9850 | 3 | 50-150 | 63 ± 1 (2) |
| D296A + F375A | 2.51 | 1.39 to 4.62 | 0.9604 | 2 | ≤30 | 56 ± 2 (1) |
| G297A + F375A | 1.34 | 0.84 to 2.20 | 0.9420 | 2 | ≤30 | |
| K298A + F375A | 1.60 | 0.87 to 3.07 | 0.9829 | 4 | 50-150 | 61 ± 0 (2) |
| D303A + F375A | 1.46 | 0.85 to 2.89 | 0.9841 | 4 | 50-150 | 62 ± 1 (1) |
| T304A + F375A | 1.51 | 0.69 to 3.34 | 0.9848 | 2 | ≤30 | 58 ± 0 (2) |
| A307G + F375A | 2.83 | 1.38 to 5.78 | 0.9569 | 1 | 50-150 | 51 ± 1 (2) |
| E341A + F375A | 2.06 | 1.53 to 2.80 | 0.9904 | 3 | 50-150 | 58 ± 1 (3) |
| H357A + F375A | 0.86 | 0.50 to 1.47 | 0.9855 | 2 | 50-150 | |
| N374A + F375A | 1.09 | 0.87 to 1.36 | 0.9968 | 2 | 50-150 | 58 ± 1 (2) |
| V376A + F375A | 1.21 | 0.93 to 1.59 | 0.9899 | 3 | 50-150 | |
| F380A + F375A | 1.39 | 0.97 to 2.11 | 0.9874 | 2 | 50-150 | 57 ± 1 (2) |
| R382A + F375A | 1.44 | 0.93 to 2.27 | 0.9957 | 2 | 50-150 | 61 ± 1 (1) |
| H10A + T304A + F375A | 1.58 | 1.13 to 2.38 | 0.9895 | 2 | 50-150 | |
| V11A + T304A + F375A | 1.29 | 0.97 to 1.74 | 0.9888 | 3 | 50-150 | |
| D30A + T304A + F375A | 1.53 | 1.12 to 2.11 | 0.9845 | 2 | 50-150 | |
| R80A + T304A + F375A | 1.50 | 0.81 to 2.75 | 0.9363 | 2 | 50-150 | |
| D82A + T304A + F375A | 1.32 | 0.85 to 2.21 | 0.9811 | 3 | 50-150 | |
| V90A + T304A + F375A | 2.07 | 1.60 to 2.68 | 0.9691 | 2 | 50-150 | |
| L111A + T304A + F375A | 1.96 | 1.33 to 2.96 | 0.9770 | 2 | 50-150 | |

TABLE 2-continued

List of constructed mutants that were screened
for half-maximal inhibitory concentration
($IC_{50}$) as also shown in FIG. 4.
Arrestin-1 mutants

| Mutant | $IC_{50}$ [M] | 95% confidence interval | Quality of fit ($R^2$) | Number of curves | Func. expression level [%] | $T_M$ (arrestin) [° C.] (No of measurements) |
|---|---|---|---|---|---|---|
| P123A + T304A + F375A | 1.02 | 1.46 to 2.79 | 0.9887 | 2 | 50-150 | |
| C143A + T304A + F375A | 1.39 | 1.16 to 1.67 | 0.9956 | 2 | 50-150 | |
| G144A + T304A + F375A | 1.93 | 1.09 to 4.68 | 0.9837 | 2 | 50-150 | |
| D146A + T304A + F375A | 1.94 | 1.57 to 2.40 | 0.9907 | 3 | 50-150 | |
| I149A + T304A + F375A | — | — | — | 3 | <detection | |
| V170A + T304A + F375A | 1.22 | 1.00 to 1.48 | 0.9988 | 2 | 50-150 | |
| L173A + T304A + F375A | 1.53 | 1.07 to 2.22 | 0.9969 | 2 | 50-150 | |
| R175A + T304A + F375A | 1.51 | 1.13 to 2.02 | 0.9784 | 1 | ≤30 | |
| V247 + T304A + F375A | 1.01 | 0.57 to 1.89 | 0.9936 | 2 | ≤30 | |
| D296A + T304A + F375A | 1.39 | 1.06 to 1.85 | 0.9941 | 2 | 50-150 | |
| G297A + T304A + F375A | 1.25 | 1.02 to 1.53 | 0.9975 | 1 | 50-150 | |
| K298A + T304A + F375A | 2.01 | 1.42 to 2.85 | 0.9832 | 3 | 50-150 | |
| D303A + T304A + F375A | 2.45 | 1.50 to 4.26 | 0.9698 | 2 | 50-150 | |
| A307G + T304A + F375A | 2.89 | 1.10 to 9.37 | 0.9446 | 2 | ≤30 | |
| E341A + T304A + F375A | 2.75 | 1.19 to 6.37 | 0.9481 | 1 | 50-150 | 61 ± 1 (2) |
| V376A + T304A + F375A | 2.14 | 1.25 to 4.39 | 0.9822 | 2 | 50-150 | |
| F380A + T304A + F375A | 2.10 | 1.00 to 5.95 | 0.9664 | 2 | 50-150 | 59 ± 1 (4) |
| R382A + T304A + F375A | 2.71 | 1.64 to 4.74 | 0.9493 | 2 | ≤30 | |
| V11A + A307G + F375A | 2.40 | 1.37 to 4.23 | 0.9591 | 1 | 50-150 | |
| R66A + A307G + F375A | 3.37 | 1.20 to 9.48 | 0.9544 | 1 | ≤30 | |
| L111A + A307G + F375A | 2.16 | 0.76 to 9.30 | 0.9842 | 2 | ≤30 | |
| P123A + A307G + F375A | 2.67 | 1.65 to 4.32 | 0.9700 | 1 | ≤30 | |
| I149A + A307G + F375A | — | — | — | 1 | <detection | |
| R175A + A307G + F375A | — | — | — | 1 | <detection | |
| V247A + A307G + F375A | 3.41 | 1.48 to 7.88 | 0.9421 | 1 | ≤30 | |
| R291A + A307G + F375A | 2.69 | 2.01 to 3.61 | 0.9883 | 1 | ≤30 | |
| D296A + A307G + F375A | 2.42 | 1.96 to 2.99 | 0.8012 | 1 | ≤30 | |
| G297A + A307G + F375A | 3.52 | 0.71 to 17.37 | 0.9228 | 1 | ≤30 | |
| V376A + A307G + F375A | 2.33 | 1.25 to 4.51 | 0.9836 | 2 | 50-150 | |
| F380A + A307G + F375A | 1.98 | 1.04 to 3.88 | 0.9062 | 2 | 50-150 | |
| R382A + A307G + F375A | 3.11 | 1.29 to 7.52 | 0.9290 | 1 | 50-150 | |
| V11A + E341A + T304A + F375A | 2.10 | 0.87 to 5.62 | 0.9660 | 3 | 50-150 | 60 ± 1 (1) |
| R66A + E341A + T304A + F375A | 2.59 | 1.07 to 6.64 | 0.9507 | 2 | 50-150 | 56 ± 1 (1) |
| R171A + E341A + T304A + F375A | 2.95 | 1.23 to 7.85 | 0.9405 | 2 | 50-150 | 59 ± 0 (1) |
| R291A + E341A + T304A + F375A | 2.10 | 1.05 to 4.31 | 0.9591 | 3 | 50-150 | 61 ± 1 (1) |
| K298A + E341A + T304A + F375A | 2.24 | 1.14 to 4.47 | 0.9741 | 3 | 50-150 | 61 ± 1 (1) |
| D303A + E341A + T304A + F375A | 2.91 | 0.85 to 9.99 | 0.9105 | 1 | 50-150 | 59 ± 1 (1) |
| R382A + E341A + T304A + F375A | 2.48 | 1.26 to 4.92 | 0.9714 | 3 | 50-150 | 56 ± 1 (1) |
| V11A + F380A + T304A + F375A | 1.63 | 1.14 to 2.33 | 0.9852 | 3 | 50-150 | |
| R66A + F380A + T304A + F375A | 2.64 | 0.80 to 8.84 | 0.9603 | 2 | 50-150 | 58 ± 0 (1) |
| F85A + F380A + T304A + F375A | 1.78 | 0.96 to 3.62 | 0.9726 | 3 | 50-150 | 61 ± 1 (1) |
| R171A + F380A + T304A + F375A | 2.07 | 0.75 to 6.59 | 0.9408 | 3 | 50-150 | 56 ± 1 (1) |
| R291A + F380A + T304A + F375A | 1.92 | 0.90 to 4.35 | 0.9714 | 2 | 50-150 | 61 ± 0 (1) |
| K298A + F380A + T304A + F375A | 1.37 | 1.02 to 1.87 | 0.9868 | 2 | 50-150 | 61 ± 0 (1) |
| D303 + F380A + T304A + F375A | 1.94 | 0.94 to 4.03 | 0.9678 | 2 | 50-150 | 60 ± 1 (1) |
| E341A + F380A + T304A + F375A | 2.00 | 0.91 to 5.39 | 0.9598 | 2 | 50-150 | 57 ± 0 (1) |

In the attached sequence protocol, the following relationships apply: arrestin-1=SEQ ID No:1, arrestin-2=SEQ ID No:2, arrestin-3=SEQ ID No:3, arrestin-4=SEQ ID No. 4, and bovine arrestin-1=SEQ ID No:5.

The invention claimed is:

1. A mutant ligand of a parent ligand, wherein said mutant ligand is mutant arrestin wherein said mutant arrestin is mutant arrestin-1, arrestin-2, arrestin-3 or arrestin-4 and said parent ligand is wild-type arrestin, wherein said wild-type arrestin is arrestin-1, arrestin-2, arrestin-3 or arrestin-4, wherein said mutant ligand has a higher binding stability with a GPCR than said parent ligand and said mutant ligand is a double mutant, triple mutant or quadruple mutant, wherein said double mutant comprises a first mutation at an amino acid position of F375 of bovine arrestin-1, (SEQ ID NO: 5) and a second mutation at an amino acid position of T304 or A307 of bovine arrestin-1, (SEQ ID NO: 5), wherein said triple mutant comprises a first mutation at an amino acid position of F375 of bovine arrestin-1, (SEQ ID NO: 5), a second mutation at an amino acid position of T304 or A307 of bovine arrestin-1, (SEQ ID NO: 5) and a third mutation at an amino acid position of H10, V11, D30, R80, D82, V90, L111, P123, C143, G144, D146, I149, V170, L173, R175, V247, D296, G297, K298, D303, A307, E341, V376, F380 or R382, of bovine arrestin-1 (SEQ ID NO:5), and wherein said quadruple mutant comprises a first mutation at an amino acid position of F375 of bovine arrestin-1, (SEQ ID NO: 5), a second mutation at an amino acid position of T304 of bovine arrestin-1, (SEQ ID NO: 5), a third mutation at an amino acid position of E341 or F380 of bovine arrestin-1 (SEQ ID NO:5) and a fourth mutation at an amino acid position of V11, R66, R171, R291, K298, D303 or R382.

2. The mutant ligand of claim 1, wherein said mutant arrestin is arrestin-1.

3. The mutant ligand of claim 1, wherein said double mutant comprises a first mutation at an amino acid position of F375 of bovine arrestin-1, (SEQ ID NO: 5) and a second mutation at an amino acid position of T304 or A307 of bovine arrestin 1, (SEQ ID NO: 5), wherein said triple mutant comprises a first mutation at an amino acid position of F375 of bovine arrestin-1, (SEQ ID NO: 5), a second mutation at an amino acid position of T304 or A307 of bovine arrestin-1, (SEQ ID NO: 5) and a third mutation at an amino acid position of R171, D303, R382, F380, or E341 of bovine arrestin-1 (SEQ ID NO:5), and wherein said quadruple mutant comprises a first mutation at an amino acid position of F375 of bovine arrestin-1, (SEQ ID NO: 5), a second mutation at an amino acid position of T304 of bovine arrestin-1, (SEQ ID NO: 5), a third mutation at an amino acid position of E341 or F380 of bovine arrestin-1 (SEQ ID NO:5) and a fourth mutation at an amino acid position of R171 or D303 of bovine arrestin-1 (SEQ ID NO:5).

4. The mutant ligand of claim 1, wherein said mutant ligand is mutated at amino acid positions of T304A+F375AA, H10A+T304A+F375A, V11A+T304A+F375A, D30A+T304A+F375A, R80A+T304A+F375A, D82A+T304A+F375A, V90A+T304A+F375A, L111A+T304A+F375A, PI23A+T304A+F375A, C143A+T304A+F375A, GI44A+T304A+F375A, DI46A+T304A+F375A, I149A+T304A+F375A, V170A+T304A+F375A, L173A+T304A+F375A, R175A+T304A+F375A, V247A+T304A+F375A, D296A+T304A+F375A, G297A+T304A+F375A, K298A+T304A+F375A, D303A+T304A+F375A, A307G+T304A+F375A, E341 A+T304A+F375A, V376A+T304A+F375A, F380A+T304A+F375A, R382A+T304A+F375A, V11A+E341A+T304A+F375A, R66A+E341A+T304A+F375A, R171A+E341A+T304A+F375A, R291A+E341A+T304A+F375A, K298A+E341 A+T304A+F375A, D303A+E341A+T304A+F375A, R382A+E341A+T304A+F375A, V11A+F380A+T304A+F375A, R66A+F380A+T304A+F375A, F85A+F380A+T304A+F375A, R171A+F380A+T304A+F375A, R291A+F380A+T304A+F375A, K298A+F380A+T304A+F375A, D303A+F380A+T304A+F375A or E34IA+F380A+T304A+F375, of bovine arrestin-1 (SEQ ID NO:5).

* * * * *

SEQUENCE LISTING

```
<160> NUMBER OF SEQ ID NOS: 5

<210> SEQ ID NO 1
<211> LENGTH: 405
<212> TYPE: PRT
<213> ORGANISM: Homo sapiens

<400> SEQUENCE: 1

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30
```

Arg Asp Tyr Ile Asp His Val Ser Gln Val Gln Pro Val Asp Gly Val
35                  40                  45

Val Leu Val Asp Pro Asp Leu Val Lys Gly Lys Val Tyr Val Thr
50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
            85                  90                  95

Pro Val Gly Ala Ala Ser Thr Pro Thr Lys Leu Gln Glu Ser Leu Leu
                100                 105                 110

Lys Lys Leu Gly Ser Asn Thr Tyr Pro Phe Leu Leu Thr Phe Pro Asp
            115                 120                 125

Tyr Leu Pro Cys Ser Val Met Leu Gln Pro Ala Pro Gln Asp Ser Gly
            130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
            195                 200                 205

Leu Ala Val Ser Leu Asn Lys Glu Ile Tyr Phe His Gly Glu Pro Ile
            210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
            275                 280                 285

Ala Asn Asn Arg Glu Arg Arg Gly Ile Ala Leu Asp Gly Lys Ile Lys
            290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
            355                 360                 365

Lys Glu Ser Tyr Gln Asp Ala Asn Leu Val Phe Glu Glu Phe Ala Arg
            370                 375                 380

His Asn Leu Lys Asp Ala Gly Glu Ala Glu Glu Gly Lys Arg Asp Lys
385                 390                 395                 400

Asn Asp Val Asp Glu
            405

<210> SEQ ID NO 2
<211> LENGTH: 418
<212> TYPE: PRT
<213> ORGANISM: Homo sapiens

```
<400> SEQUENCE: 2

Met Gly Asp Lys Gly Thr Arg Val Phe Lys Lys Ala Ser Pro Asn Gly
1               5                   10                  15

Lys Leu Thr Val Tyr Leu Gly Lys Arg Asp Phe Val Asp His Ile Asp
            20                  25                  30

Leu Val Asp Pro Val Asp Gly Val Val Leu Val Asp Pro Glu Tyr Leu
        35                  40                  45

Lys Glu Arg Arg Val Tyr Val Thr Leu Thr Cys Ala Phe Arg Tyr Gly
    50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
                85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
        115                 120                 125

Leu Gln Pro Gly Pro Glu Asp Thr Gly Lys Ala Cys Gly Val Asp Tyr
    130                 135                 140

Glu Val Lys Ala Phe Cys Ala Glu Asn Leu Glu Glu Lys Ile His Lys
145                 150                 155                 160

Arg Asn Ser Val Arg Leu Val Ile Arg Lys Val Gln Tyr Ala Pro Glu
                165                 170                 175

Arg Pro Gly Pro Gln Pro Thr Ala Glu Thr Thr Arg Gln Phe Leu Met
            180                 185                 190

Ser Asp Lys Pro Leu His Leu Glu Ala Ser Leu Asp Lys Glu Ile Tyr
        195                 200                 205

Tyr His Gly Glu Pro Ile Ser Val Asn Val His Val Thr Asn Asn Thr
    210                 215                 220

Asn Lys Thr Val Lys Lys Ile Lys Ile Ser Val Arg Gln Tyr Ala Asp
225                 230                 235                 240

Ile Cys Leu Phe Asn Thr Ala Gln Tyr Lys Cys Pro Val Ala Met Glu
                245                 250                 255

Glu Ala Asp Asp Thr Val Ala Pro Ser Ser Thr Phe Cys Lys Val Tyr
            260                 265                 270

Thr Leu Thr Pro Phe Leu Ala Asn Asn Arg Glu Lys Arg Gly Leu Ala
        275                 280                 285

Leu Asp Gly Lys Leu Lys His Glu Asp Thr Asn Leu Ala Ser Ser Thr
    290                 295                 300

Leu Leu Arg Glu Gly Ala Asn Arg Glu Ile Leu Gly Ile Ile Val Ser
305                 310                 315                 320

Tyr Lys Val Lys Val Lys Leu Val Val Ser Arg Gly Gly Leu Leu Gly
                325                 330                 335

Asp Leu Ala Ser Ser Asp Val Ala Val Glu Leu Pro Phe Thr Leu Met
            340                 345                 350

His Pro Lys Pro Lys Glu Glu Pro Pro His Arg Glu Val Pro Glu Asn
        355                 360                 365

Glu Thr Pro Val Asp Thr Asn Leu Ile Glu Leu Asp Thr Asn Asp Asp
    370                 375                 380

Asp Ile Val Phe Glu Asp Phe Ala Arg Gln Arg Leu Lys Gly Met Lys
385                 390                 395                 400

Asp Asp Lys Glu Glu Glu Asp Gly Thr Gly Ser Pro Gln Leu Asn
                405                 410                 415
```

Asn Arg

<210> SEQ ID NO 3
<211> LENGTH: 409
<212> TYPE: PRT
<213> ORGANISM: Homo sapiens

<400> SEQUENCE: 3

```
Met Gly Glu Lys Pro Gly Thr Arg Val Phe Lys Ser Ser Pro Asn
1               5                   10                  15

Cys Lys Leu Thr Val Tyr Leu Gly Lys Arg Asp Phe Val Asp His Leu
                20                  25                  30

Asp Lys Val Asp Pro Val Asp Gly Val Val Leu Val Asp Pro Asp Tyr
            35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
            180                 185                 190

Met Ser Asp Arg Ser Leu His Leu Glu Ala Ser Leu Asp Lys Glu Leu
        195                 200                 205

Tyr Tyr His Gly Glu Pro Leu Asn Val Asn Val His Val Thr Asn Asn
210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
            260                 265                 270

Tyr Thr Ile Thr Pro Leu Leu Ser Asp Asn Arg Glu Lys Arg Gly Leu
        275                 280                 285

Ala Leu Asp Gly Lys Leu Lys His Glu Asp Thr Asn Leu Ala Ser Ser
290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
            340                 345                 350
```

```
Ile Pro Leu Pro Arg Pro Gln Ser Ala Ala Pro Glu Thr Asp Val Pro
        355                 360                 365

Val Asp Thr Asn Leu Ile Glu Phe Asp Thr Asn Tyr Ala Thr Asp Asp
    370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys
                405

<210> SEQ ID NO 4
<211> LENGTH: 388
<212> TYPE: PRT
<213> ORGANISM: Homo sapiens

<400> SEQUENCE: 4

Met Ser Lys Val Phe Lys Lys Thr Ser Ser Asn Gly Lys Leu Ser Ile
1               5                   10                  15

Tyr Leu Gly Lys Arg Asp Phe Val Asp His Val Asp Thr Val Glu Pro
            20                  25                  30

Ile Asp Gly Val Val Leu Val Asp Pro Glu Tyr Leu Lys Cys Arg Lys
        35                  40                  45

Leu Phe Val Met Leu Thr Cys Ala Phe Arg Tyr Gly Arg Asp Asp Leu
    50                  55                  60

Glu Val Ile Gly Leu Thr Phe Arg Lys Asp Leu Tyr Val Gln Thr Leu
65                  70                  75                  80

Gln Val Val Pro Ala Glu Ser Ser Pro Gln Gly Pro Leu Thr Val
                85                  90                  95

Leu Gln Glu Arg Leu Leu His Lys Leu Gly Asp Asn Ala Tyr Pro Phe
                100                 105                 110

Thr Leu Gln Met Val Thr Asn Leu Pro Cys Ser Val Thr Leu Gln Pro
                115                 120                 125

Gly Pro Glu Asp Ala Gly Lys Pro Cys Gly Ile Asp Phe Glu Val Lys
            130                 135                 140

Ser Phe Cys Ala Glu Asn Pro Glu Glu Thr Val Ser Lys Arg Asp Tyr
145                 150                 155                 160

Val Arg Leu Val Val Arg Lys Val Gln Phe Ala Pro Pro Glu Ala Gly
                165                 170                 175

Pro Gly Pro Ser Ala Gln Thr Ile Arg Arg Phe Leu Leu Ser Ala Gln
            180                 185                 190

Pro Leu Gln Leu Gln Ala Trp Met Asp Arg Glu Val His Tyr His Gly
            195                 200                 205

Glu Pro Ile Ser Val Asn Val Ser Ile Asn Asn Cys Thr Asn Lys Val
        210                 215                 220

Ile Lys Lys Ile Lys Ile Ser Val Asp Gln Ile Thr Asp Val Val Leu
225                 230                 235                 240

Tyr Ser Leu Asp Lys Tyr Thr Lys Thr Val Phe Ile Gln Glu Phe Thr
                245                 250                 255

Glu Thr Val Ala Ala Asn Ser Ser Phe Ser Gln Ser Phe Ala Val Thr
            260                 265                 270

Pro Ile Leu Ala Ala Ser Cys Gln Lys Arg Gly Leu Ala Leu Asp Gly
        275                 280                 285

Lys Leu Lys His Glu Asp Thr Asn Leu Ala Ser Ser Thr Ile Ile Arg
    290                 295                 300
```

```
Pro Gly Met Asp Lys Glu Leu Leu Gly Ile Leu Val Ser Tyr Lys Val
305                 310                 315                 320

Arg Val Asn Leu Met Val Ser Cys Gly Gly Ile Leu Gly Asp Leu Thr
            325                 330                 335

Ala Ser Asp Val Gly Val Glu Leu Pro Leu Val Leu Ile His Pro Lys
        340                 345                 350

Pro Ser His Glu Ala Ala Ser Ser Glu Asp Ile Val Ile Glu Glu Phe
    355                 360                 365

Thr Arg Lys Gly Glu Glu Ser Gln Lys Ala Val Glu Ala Glu Gly
370                 375                 380

Asp Glu Gly Ser
385

<210> SEQ ID NO 5
<211> LENGTH: 404
<212> TYPE: PRT
<213> ORGANISM: Bos taurus

<400> SEQUENCE: 5

Met Lys Ala Asn Lys Pro Ala Pro Asn His Val Ile Phe Lys Lys Ile
1               5                   10                  15

Ser Arg Asp Lys Ser Val Thr Ile Tyr Leu Gly Lys Arg Asp Tyr Ile
            20                  25                  30

Asp His Val Glu Arg Val Glu Pro Val Asp Gly Val Val Leu Val Asp
        35                  40                  45

Pro Glu Leu Val Lys Gly Lys Arg Val Tyr Val Ser Leu Thr Cys Ala
    50                  55                  60

Phe Arg Tyr Gly Gln Glu Asp Ile Asp Val Met Gly Leu Ser Phe Arg
65                  70                  75                  80

Arg Asp Leu Tyr Phe Ser Gln Val Gln Val Phe Pro Pro Val Gly Ala
                85                  90                  95

Ser Gly Ala Thr Thr Arg Leu Gln Glu Ser Leu Ile Lys Lys Leu Gly
            100                 105                 110

Ala Asn Thr Tyr Pro Phe Leu Leu Thr Phe Pro Asp Tyr Leu Pro Cys
        115                 120                 125

Ser Val Met Leu Gln Pro Ala Pro Gln Asp Val Gly Lys Ser Cys Gly
    130                 135                 140

Val Asp Phe Glu Ile Lys Ala Phe Ala Thr His Ser Thr Asp Val Glu
145                 150                 155                 160

Glu Asp Lys Ile Pro Lys Lys Ser Ser Val Arg Leu Leu Ile Arg Lys
                165                 170                 175

Val Gln His Ala Pro Arg Asp Met Gly Pro Gln Pro Arg Ala Glu Ala
            180                 185                 190

Ser Trp Gln Phe Phe Met Ser Asp Lys Pro Leu Arg Leu Ala Val Ser
    195                 200                 205

Leu Ser Lys Glu Ile Tyr Tyr His Gly Glu Pro Ile Pro Val Thr Val
210                 215                 220

Ala Val Thr Asn Ser Thr Glu Lys Thr Val Lys Lys Ile Lys Val Leu
225                 230                 235                 240

Val Glu Gln Val Thr Asn Val Val Leu Tyr Ser Ser Asp Tyr Tyr Ile
                245                 250                 255

Lys Thr Val Ala Ala Glu Glu Ala Gln Glu Lys Val Pro Pro Asn Ser
            260                 265                 270
```

-continued

```
Ser Leu Thr Lys Thr Leu Thr Leu Val Pro Leu Leu Ala Asn Asn Arg
        275                 280                 285

Glu Arg Arg Gly Ile Ala Leu Asp Gly Lys Ile Lys His Glu Asp Thr
    290                 295                 300

Asn Leu Ala Ser Ser Thr Ile Ile Lys Glu Gly Ile Asp Lys Thr Val
305                 310                 315                 320

Met Gly Ile Leu Val Ser Tyr Gln Ile Lys Val Lys Leu Thr Val Ser
                325                 330                 335

Gly Leu Leu Gly Glu Leu Thr Ser Ser Glu Val Ala Thr Glu Val Pro
                340                 345                 350

Phe Arg Leu Met His Pro Gln Pro Glu Asp Pro Asp Thr Ala Lys Glu
        355                 360                 365

Ser Phe Gln Asp Glu Asn Phe Val Phe Glu Glu Phe Ala Arg Gln Asn
    370                 375                 380

Leu Lys Asp Ala Gly Glu Tyr Lys Glu Glu Lys Thr Asp Gln Glu Ala
385                 390                 395                 400

Ala Met Asp Glu
```